United States Patent
Thomas et al.

(10) Patent No.: US 11,267,880 B2
(45) Date of Patent: Mar. 8, 2022

(54) ANTI-SEMA3A ANTIBODIES AND THEIR USES FOR TREATING EYE OR OCULAR DISEASES

(71) Applicant: Boehringer Ingelheim International GmbH, Ingelheim am Rhein (DE)

(72) Inventors: Leo Thomas, Biberach an der Riss (DE); Rachel Rebecca Barrett, Bethel, CT (US); Kristin Laura Bovat, Ridgefield, CT (US); Rajkumar Ganesan, Blue Bell, PA (US); Priyanka Gupta, Danbury, CT (US); Fei Han, Sandy Hook, CT (US); Dongmei Liu, Oxford, CT (US); Juergen Prestle, Biberach an der Riss (DE); Sanjaya Singh, Blue Bell, PA (US); Sathyadevi Venkataramani, Blue Bell, PA (US); Helen Haixia Wu, Danbury, CT (US); Nina Zippel, Biberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 38 days.

(21) Appl. No.: 16/869,618

(22) Filed: May 8, 2020

(65) Prior Publication Data
US 2020/0385446 A1 Dec. 10, 2020

(30) Foreign Application Priority Data
May 9, 2019 (EP) .................................. 19173454

(51) Int. Cl.
*C07K 16/18* (2006.01)
*A61K 38/17* (2006.01)
*C07K 14/47* (2006.01)
*A61P 25/28* (2006.01)
*A61K 9/00* (2006.01)

(52) U.S. Cl.
CPC ............ *C07K 16/18* (2013.01); *A61K 9/0048* (2013.01); *C07K 2317/565* (2013.01)

(58) Field of Classification Search
None
See application file for complete search history.

(56) References Cited

U.S. PATENT DOCUMENTS

2015/0368327 A1 12/2015 Goshima et al.
2018/0244775 A1 8/2018 Nam et al.

FOREIGN PATENT DOCUMENTS

| EP | 2955195 A1 | 12/2015 |
| EP | 3385281 A1 | 10/2018 |
| WO | 13005603 A1 | 1/2013 |
| WO | 14127479 A1 | 8/2014 |
| WO | 2020225400 A1 | 11/2020 |

OTHER PUBLICATIONS

Yamashita, The JapaneseSociety for Immunolgy, Anti-Semaphorin 3A neutralization monoclonal antibody prevents sepsis development in lipopolysacchaaride-treated mice, vol. 27, 2015.

(Continued)

*Primary Examiner* — Aurora M Fontainhas
(74) *Attorney, Agent, or Firm* — David L. Kershner

(57) ABSTRACT

The present invention relates to antibodies and fragments thereof that target semaphorin 3A (Sema3A). More specifically, anti-Sema3A antibodies and methods of use for the treatment of various diseases or disorders are disclosed.

26 Claims, 4 Drawing Sheets
Specification includes a Sequence Listing.

(56) References Cited

OTHER PUBLICATIONS

Shirvan, The J. of Biological Chem., Anti-Semaphorin 3a Antibodies Rescue Retinal Ganglion cells from Cell Death, vol. 27, 2002.
Yuan, Oncotarget, A mechanism for semaphorin-induced apoptosis: DNA damage of endothelial and myogenic cells in primary cultures from skeletal muscle, vol. 9, 2018.
Abstract for WO2013005603 cited herein.
Giacobini, PLOS, Brain Endothelial Cells Control Fertility through Ovarian Steroid dependent release of Semaphoran 3A, vol. 12, 2014.
International Search Report and Written Opinion dated Jul. 17, 2020 for PCT/EP2020062802.
Guo, Aqueous Semaphoring 3A level correlates with retinal macular oedema and ganglion cell degeneration in patients, Acta Opthamologica, vol. 97, 2019.
Joyal, Ischemic Meurons prevent vascular regeneration of neural tissue, Blood, vol. 117, 2011.

ANTI-SEMA3A ANTIBODIES AND THEIR USES FOR TREATING EYE OR OCULAR DISEASES

SEQUENCE LISTING

The instant application contains a Sequence Listing which has been submitted electronically in ASCII format and is hereby incorporated by reference in its entirety. Said ASCII copy, created on Jul. 9, 2020, is named 01-3361-US-1_SL.txt and is 38,591 bytes in size.

FIELD OF THE INVENTION

This invention generally relates to antibodies and fragments thereof that target semaphorin 3A (Sema3A). More specifically, anti-Sema3A antibodies and methods of use for the treatment of various diseases or disorders are disclosed. Pharmaceutical compositions and kits comprising the anti-Sema3A antibody are also disclosed.

BACKGROUND OF THE INVENTION

Ischemic retinopathies are characterized by loss or dysfunction of the retinal vasculature, which results in a reduction of blood flow and hypoxia. Ischemia of the retina results in up-regulation of proangiogenic growth factors that promote retinal neovascularization, which can lead to blindness. However, revascularization of the ischemic retina does not occur, when there is robust pathologic neovascularization into the vitreous, a region of the eye normally devoid of blood vessels.

The growth of these abnormal new vessels creates most of the threat to vision since they can leak, lead to hemorrhage or lead to scarring that may end in retinal detachment. Current treatments for ischemic retinopathies seek to halt the growth of the pathological vessels but do not address the underlying ischemia that drives their growth. Furthermore, standard treatment for diabetic retinopathy involves destruction of a portion of the retina with a laser in an attempt to stop new vessel growth and preserve central vision. These treatments are however to some extent inefficient. While some patients may maintain a stable vision for many years, a high percentage of patients suffering from retinopathy eventually suffers from total visual loss.

Consequently, there is still an unfulfilled need for new therapeutic approaches for efficiently treating eye or retinal diseases.

SUMMARY OF THE INVENTION

Sema3A is an endogenous secreted protein that belongs to the class 3 semaphorin family (Sema3), which were originally identified as axonal guidance molecules and were implicated in vessel pathfinding and network formation. Neuropilin 1 and 2 (Nrp1 and Nrp2) and the type A/D plexins (Plxns) act as the ligands binding and the signal transducing subunits of the Sema3 receptor complexes on the surface of endothelial cells (ECs). As a special member of the Sema3 family, Sema3A binds to Nrp1 exclusively at first and then combines with PlexinA1-4 as a complex (Nrp1/PlexA1-4). In this receptor complex, Nrp1 acts as a binding element, while PlexA1-4 acts as a signal-transducing element.

Human Semaphorin 3A is a protein as disclosed in SEQ ID NO: 22 and available under the NCBI Reference Sequence NP_006071.1. Further, human Sema3A is encoded by the Gene ID: 10371 (NCBI).

Sema3A has been studied in tumor angiogenesis and metastasis for years, but its effects on retinal neovascularization are still unclear. The inventors have exemplified that Semaphorin 3A is secreted by hypoxic retinal ganglion cells and acts as a vasorepulsive cue. Sema3A repels neovessels away from ischemic region by inducing a cytoskeletal collapse in these cells. Without wishing to be bound by theory, the inventors have hypothesized that this would explain why revascularization of ischemic regions does not occur and instead the up-regulation of Sema3A leads to a pathological neovascularisation into the vitreous region.

Semaphorin 3A is secreted by hypoxic neurons in ischemic/avascular retina, thereby inhibiting vascular regeneration of the retina and enhancing pathologic preretinal neovascularization.

The inventors have addressed this pathological situation by developing antibodies targeting Sema3A. The present invention thus provides monoclonal antibodies that specifically bind to Sema3A, preferably human Sema3A.

In a first aspect, the present invention provides an anti-Sema3A antibody or an antigen-binding fragment thereof comprising:
  a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
  a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In another embodiment, the present invention provides an anti-Sema3A antibody or an antigen-binding fragment thereof comprising:
  a heavy chain variable region comprising an amino acid sequence at least 80%, at least 90%, at least 95%, at least 98%, or at least 99% identical to the amino acid sequence SEQ ID NO: 7, SEQ ID NO: 8, SEQ ID NO: 9 or SEQ ID NO: 10; and
  a light chain variable region comprising an amino acid sequence at least 80%, at least 90%, at least 95%, at least 98%, or at least 99% identical to the amino acid sequence of SEQ ID NO: 11, SEQ ID NO: 12 or SEQ ID NO: 13;
wherein:
  the heavy chain variable region comprises the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
  the light chain variable region comprises the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In another embodiment, the present invention provides an anti-Sema3A antibody or an antigen-binding fragment thereof comprising:
  a heavy chain variable region comprising an amino acid sequence at least 80%, at least 90%, at least 95%, at least 98%, or at least 99% identical to the amino acid sequence SEQ ID NO: 7, SEQ ID NO: 8, SEQ ID NO: 9 or SEQ ID NO: 10; and
  a light chain variable region comprising an amino acid sequence at least 80%, at least 90%, at least 95%, at least 98%, or at least 99% identical to the amino acid sequence of SEQ ID NO: 11, SEQ ID NO: 12 or SEQ ID NO: 13.

In yet another embodiment, the present invention provides an anti-Sema3A antibody or an antigen-binding fragment thereof comprising:
  a heavy chain variable region comprising the amino acid sequences of SEQ ID NO: 7, SEQ ID NO: 8, SEQ ID NO: 9 or SEQ ID NO: 10; and
  a light chain variable region comprising the amino acid sequence of SEQ ID NO: 11, SEQ ID NO: 12 or SEQ ID NO: 13.

In another embodiment, the present invention provides an anti-Sema3A antibody or an antigen-binding fragment thereof comprising:
  a. a variable heavy chain and a variable light chain comprising the amino acid sequences of SEQ ID NO: 7 and SEQ ID NO: 11, respectively;
  b. a variable heavy chain and a variable light chain comprising the amino acid sequences of SEQ ID NO: 8 and SEQ ID NO: 11, respectively;
  c. a variable heavy chain and a variable light chain comprising the amino acid sequences of SEQ ID NO: 9 and SEQ ID NO: 12, respectively; or
  d. a variable heavy chain and a variable light chain comprising the amino acid sequences of SEQ ID NO: 10 and SEQ ID NO: 13, respectively.

In yet another embodiment, the present invention provides an anti-Sema3A antibody or an antigen-binding fragment thereof comprising:
  a heavy chain comprising, preferably consisting of, the amino acid sequence of SEQ ID NO: 14, SEQ ID NO: 16, SEQ ID NO: 17, or SEQ ID NO: 19; and
  a light chain comprising, preferably consisting of, the amino acid sequence of SEQ ID NO: 15, SEQ ID NO: 18 or SEQ ID NO: 20.

In a particular embodiment, the invention relates to an anti-Sema3A antibody or an antigen-binding fragment thereof comprising:
  a. a heavy chain comprising the amino acid sequence of SEQ ID NO: 14 and a light chain comprising the amino acid sequence of SEQ ID NO: 15;
  b. a heavy chain comprising the amino acid sequence of SEQ ID NO: 16 and a light chain comprising the amino acid sequence of SEQ ID NO: 15;
  c. a heavy chain comprising the amino acid sequence of SEQ ID NO: 17 and a light chain comprising the amino acid sequence of SEQ ID NO: 18; or
  d. a heavy chain comprising the amino acid sequence of SEQ ID NO: 19 and a light chain comprising the amino acid sequence of SEQ ID NO: 20.

In a particular preferred embodiment, the anti-Sema3A antibody is a humanized anti-Sema3A antibody.

In a second aspect, the present invention provides an anti-Sema3A antibody or an antigen-binding fragment thereof that binds to at least one amino acid residue within amino acid regions 370-382 of the human Sema3A as depicted in SEQ ID NO: 22.

In one embodiment, the present invention provides an anti-Sema3A antibody or an antigen-binding fragment thereof that binds to at least one amino acid residue within amino acid regions as set forth in SEQ ID NO: 21 (DSTKDLPDDVITF). In a preferred embodiment, the present invention provides an anti-Sema3A antibody or an antigen-binding fragment thereof that binds the amino acid regions as set forth in SEQ ID NO: 21.

In a third aspect, the present invention provides an anti-Sema3A antibody or an antigen-binding fragment thereof for use as a medicament.

In one embodiment, the present invention provides an anti-Sema3A or an antigen-binding fragment for inhibiting the vasorepressive effect of SemaA, and/or for improving revascularisation of the retina.

In one embodiment, the present invention provides an anti-Sema3A antibody or an antigen-binding fragment thereof for use in the treatment or prevention of a retinal or eye disease.

In a fourth aspect, the present invention provides an anti-Sema3A antibody or an antigen-binding fragment thereof for use in the treatment or prevention of a disease selected from the group consisting of retinopathy, ischemic retinopathy, diabetic retinopathy including proliferative diabetic retinopathy and non-proliferative diabetic retinopathy, diabetic macular edema, diabetic macular ischemia, age-related macular degeneration, retinitis pigmentosa, inherited retinal dystrophy, myopic degeneration, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease.

In another embodiment, the present invention provides an anti-Sema3A antibody or an antigen-binding fragment thereof for use in the treatment or prevention of a disease selected from the group consisting of diabetic retinopathy including proliferative diabetic retinopathy and non-proliferative diabetic retinopathy, ischemic retinopathy, diabetic macular edema, diabetic macular ischemia, age-related macular edema, retinal neovascularization, glaucoma and choroidal neovascularization. Preferably, said disease is diabetic macular edema and/or diabetic macular ischemia.

In a preferred embodiment, the present invention provides an anti-Sema3A antibody or an antigen-binding fragment thereof for use in the treatment of diabetic macular ischemia, by promoting vascular regeneration within the ischemic retina (revascularization) and preventing pathological neovascularization of the vitreous region of the eye.

In another preferred embodiment, the present invention provides an anti-Sema3A antibody or an antigen-binding fragment thereof for use in the treatment of diabetic macular edema, by reducing permeability of blood retinal barrier.

In another preferred embodiment, the present invention provides an anti-Sema3A antibody or an antigen-binding fragment thereof for inhibiting Sema3A-induced permeability of the blood retinal barrier and/or Sema3A-induced vasoregression from ischemic areas.

In a fifth aspect, the present invention provides a pharmaceutical composition comprising an anti-Sema3A antibody or an antigen-binding fragment thereof and a pharmaceutically acceptable carrier.

In one embodiment, the present invention provides an anti-Sema3A antibody or an antigen-binding fragment thereof or a pharmaceutical composition comprising an anti-Sema3A antibody or an antigen-binding fragment thereof, wherein said antibody or an antigen-binding fragment thereof is administered by a parenteral route, intravenous route, intravitreal route or subcutaneous route of administration, preferably by intravitreal route.

In a sixth aspect, the present invention provides an isolated polynucleotide or polynucleotides comprising:
  a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 15, SEQ ID NO: 18 or SEQ ID NO: 20 or a light chain variable region as shown in SEQ ID NO: 11, SEQ ID NO: 12 or SEQ ID NO: 13.

In one embodiment, the present invention provides an expression vector comprising an isolated polynucleotide or polynucleotides comprising a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 15, SEQ ID NO: 18 or SEQ ID NO: 20 or a light chain variable region as shown in SEQ ID NO: 11, SEQ ID NO: 12 or SEQ ID NO: 13.

In one embodiment, the present invention provides a viral vector comprising an isolated polynucleotide or polynucleotides comprising a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 15, SEQ ID NO: 18 or SEQ ID NO: 20 or a light chain variable region as shown in SEQ ID NO: 11, SEQ ID NO: 12 or SEQ ID NO: 13.

In one embodiment, the present invention provides a host cell comprising an expression vector or an isolated polynucleotide or polynucleotides comprising a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 15, SEQ ID NO: 18 or SEQ ID NO: 20 or a light chain variable region as shown in SEQ ID NO: 11, SEQ ID NO: 12 or SEQ ID NO: 13.

In one embodiment, the present invention provides a method for producing an anti-Sema3A antibody or an antigen-binding fragment thereof comprising obtaining a host cell comprising an expression vector or an isolated polynucleotide or polynucleotides comprising a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 7, SEQ ID NO: 8, SEQ ID NO: 9 or SEQ ID NO: 10 or a light chain variable region as shown in SEQ ID NO: 11, SEQ ID NO: 12 or SEQ ID NO: 13; and cultivating the host cell.

In one embodiment, the method for producing an anti-Sema3A antibody or an antigen-binding fragment thereof further comprises recovering and purifying the anti-Sema3A antibody or an antigen-binding fragment thereof.

BRIEF DESCRIPTION OF THE DRAWINGS

FIG. 1A shows the localization of Sema3A in human eyes in prespecified retinal samples from human donors with a history of Diabetic Retinopathy or primary open angle glaucoma (POAG) in comparison to age matched controls (Age ctrl) and subjects with Diabetes, but no ocular pathology (DM ctrl). Sema3A was found in the vasculature wall of retinal blood vessels.

FIG. 1B shows unidentified but distinctive Sema3A fluorescent objects were observed in the retinal ganglion cell layer.

Figure 4A:
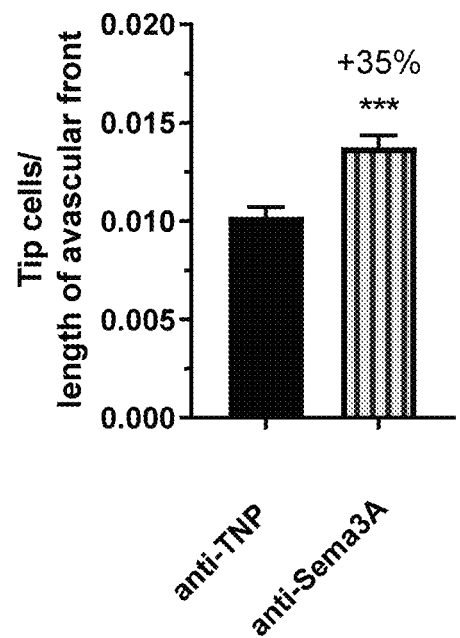
FIGS. 4A, 4B and 4C show the efficacy on tip cell density and avascular area in vivo.
Figure 4B:
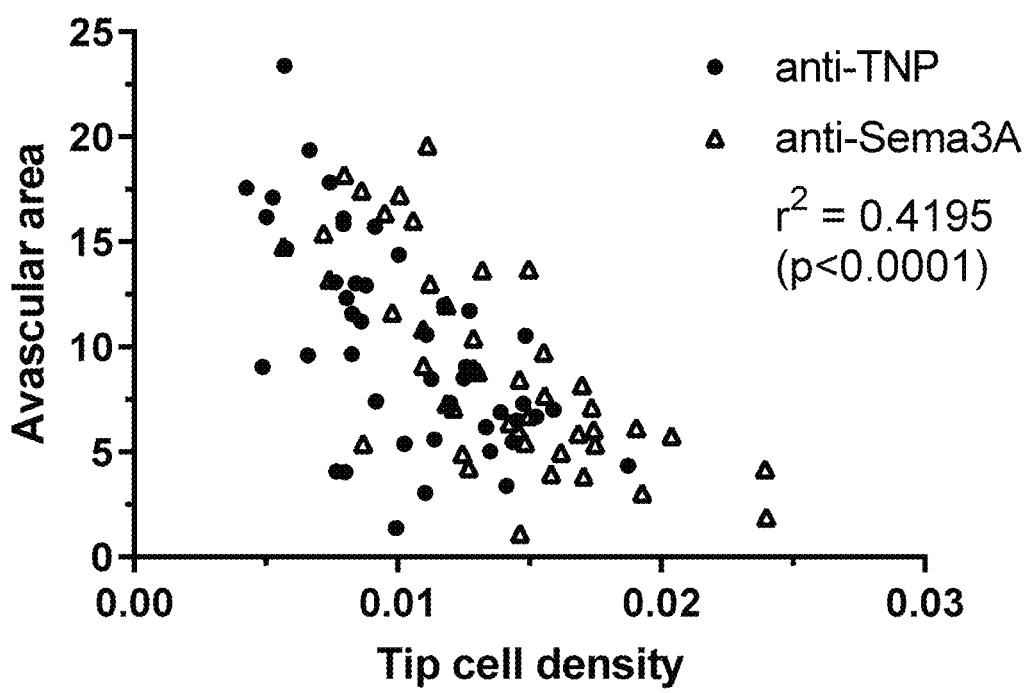

Tip cell density (FIG. 4A) and avascular area (FIG. 4B) were investigated in a model of oxygen-induced retinopathy in mouse pups. Animals were exposed 75% oxygen from P7 to P12 and received a single intravitreal injection of antibody after returning to normoxia on P12. Anti-TNP is a control antibody against trinitrophenol. Anti-Sema3A is an antibody according to the invention (clone I). On P17, retinal flatmounts were prepared, stained with isolectin B4 and used for counting of tip cells and determination of the size of the retinal avascular area.

Figure 4C:
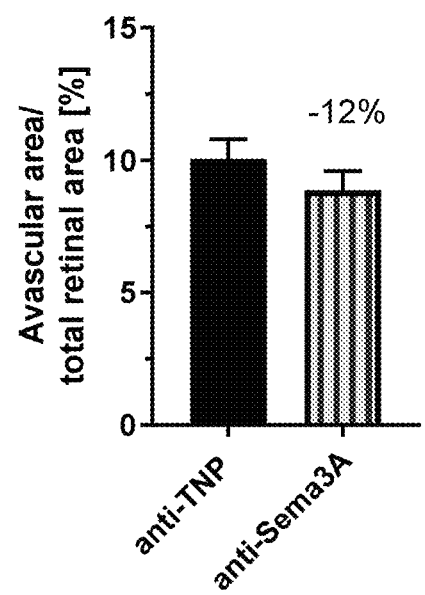

FIG. 4C shows the correlation between the tip cell density and avascular area is shown.

DETAILED DESCRIPTION OF THE INVENTION

Definitions

The generalized structure of antibodies or immunoglobulin is well known to the person skilled in the art, these molecules are heterotetrameric glycoproteins, typically of about 150,000 daltons, composed of two identical light (L) chains and two identical heavy (H) chains. Each light chain is covalently linked to a heavy chain by one disulfide bond to form a heterodimer, and the heterotrimeric molecule is formed through a covalent disulfide linkage between the two identical heavy chains of the heterodimers. Although the light and heavy chains are linked together by one disulfide bond, the number of disulfide linkages between the two heavy chains varies by immunoglobulin isotype. Each heavy and light chain also has regularly spaced intrachain disulfide bridges. Each heavy chain has at the amino-terminus a variable domain ($V_H$=variable heavy chain), followed by three or four constant domains ($C_{H1}$, $C_{H2}$, $C_{H3}$, and $C_{H4}$), as well as a hinge region between $C_{H1}$ and $C_{H2}$. Each light chain has two domains, an amino-terminal variable domain ($V_L$=variable light chain) and a carboxy-terminal constant domain ($C_L$). The $V_L$ domain associates non-covalently with the $V_H$ domain, whereas the $C_L$ domain is commonly covalently linked to the $C_{H1}$ domain via a disulfide bond. Particular amino acid residues are believed to form an interface between the light and heavy chain variable domains (Chothia et al., 1985, J. Mol. Biol. 186:651-663.)

Certain domains within the variable domains differ extensively between different antibodies i.e., are "hypervariable." These hypervariable domains contain residues that are directly involved in the binding and specificity of each particular antibody for its specific antigenic determinant. Hypervariability, both in the light chain and the heavy chain variable domains, is concentrated in three segments known as complementarity determining regions (CDRs) or hypervariable loops (HVLs). CDRs are defined by sequence comparison in Kabat et al., 1991, In: Sequences of Proteins of Immunological Interest, $5^{th}$ Ed. Public Health Service, National Institutes of Health, Bethesda, Md., whereas HVLs are structurally defined according to the three-dimensional structure of the variable domain, as described by Chothia and Lesk, 1987, J. Mol. Biol. 196: 901-917. Where these two methods result in slightly different identifications of a CDR, the structural definition is preferred. As defined by Kabat, CDR-L1 is positioned at about residues 24-34, CDR-L2, at about residues 50-56, and CDR-L3, at about residues 89-97 in the light chain variable domain; CDR-H1 is positioned at about residues 31-35, CDR-H2 at about residues 50-65, and CDR-H3 at about residues 95-102 in the heavy chain variable domain. The CDR1, CDR2, CDR3 of the heavy and light chains therefore define the unique and functional properties specific for a given antibody.

The three CDRs within each of the heavy and light chains are separated by framework regions (FR), which contain sequences that tend to be less variable. From the amino terminus to the carboxy terminus of the heavy and light chain variable domains, the FRs and CDRs are arranged in the order: FR1, CDR1, FR2, CDR2, FR3, CDR3, and FR4. The largely β-sheet configuration of the FRs brings the CDRs within each of the chains into close proximity to each other as well as to the CDRs from the other chain. The resulting conformation contributes to the antigen binding site (see Kabat et al., 1991, NIH Publ. No. 91-3242, Vol. I, pages 647-669), although not all CDR residues are necessarily directly involved in antigen binding.

FR residues and Ig constant domains are not directly involved in antigen binding, but contribute to antigen binding and/or mediate antibody effector function. Some FR residues are thought to have a significant effect on antigen binding in at least three ways: by noncovalently binding directly to an epitope, by interacting with one or more CDR residues, and by affecting the interface between the heavy and light chains. The constant domains are not directly involved in antigen binding but mediate various Ig effector functions, such as participation of the antibody in antibody-dependent cellular cytotoxicity (ADCC), complement-dependent cytotoxicity (CDC) and antibody-dependent cellular phagocytosis (ADCP).

The light chains of vertebrate immunoglobulins are assigned to one of two clearly distinct classes, kappa (κ) and lambda (λ), based on the amino acid sequence of the constant domain. By comparison, the heavy chains of mammalian immunoglobulins are assigned to one of five major classes, according to the sequence of the constant domains: IgA, IgD, IgE, IgG, and IgM. IgG and IgA are further divided into subclasses (isotypes), e.g., $IgG_1$, $IgG_2$, $IgG_3$, $IgG_4$, $IgA_1$, and $IgA_2$, respectively. The heavy chain constant domains that correspond to the different classes of immunoglobulins are called α, δ, ε, γ, and μ, respectively. The subunit structures and three-dimensional configurations of the classes of native immunoglobulins are well known.

The terms, "antibody", "anti-Sema3A antibody", "humanized anti-Sema3A antibody", and "variant humanized anti-Sema3A antibody" are used herein in the broadest sense and specifically encompass monoclonal antibodies (including full length monoclonal antibodies), multispecific antibodies (e.g., bispecific antibodies), and antibody fragments such as variable domains and other portions of antibodies that exhibit a desired biological activity, e.g., binding to Sema3A.

The term "monoclonal antibody" (mAb) refers to an antibody of a population of substantially homogeneous antibodies; that is, the individual antibodies in that population are identical except for naturally occurring mutations that may be present in minor amounts. Monoclonal antibodies are highly specific, being directed against a single antigenic determinant, an "epitope". Therefore, the modifier "monoclonal" is indicative of a substantially homogeneous population of antibodies directed to the identical epitope and is not to be construed as requiring production of the antibody by any particular method. It should be understood that monoclonal antibodies can be made by any technique or methodology known in the art; including e.g., the hybridoma method (Kohler et al., 1975, Nature 256:495), or recombinant DNA methods known in the art (see, e.g., U.S. Pat. No. 4,816,567), or methods of isolation of monoclonal recombinantly produced using phage antibody libraries, using techniques described in Clackson et al., 1991, Nature 352: 624-628, and Marks et al., 1991, J. Mol. Biol. 222: 581-597.

Chimeric antibodies consist of the heavy and light chain variable regions of an antibody from one species (e.g., a non-human mammal such as a mouse) and the heavy and light chain constant regions of another species (e.g. human) antibody and can be obtained by linking the DNA sequences encoding the variable regions of the antibody from the first species (e.g., mouse) to the DNA sequences for the constant regions of the antibody from the second (e.g. human) species and transforming a host with an expression vector containing the linked sequences to allow it to produce a chimeric antibody. Alternatively, the chimeric antibody also could be one in which one or more regions or domains of the heavy and/or light chain is identical with, homologous to, or a variant of the corresponding sequence in a monoclonal antibody from another immunoglobulin class or isotype, or from a consensus or germline sequence. Chimeric antibodies can include fragments of such antibodies, provided that the antibody fragment exhibits the desired biological activity of its parent antibody, for example binding to the same epitope (see, e.g., U.S. Pat. No. 4,816,567; and Morrison et al., 1984, Proc. Natl. Acad. Sci. USA 81: 6851-6855).

The terms, "antibody fragment", "antigen binding fragment", "anti-Sema3A antibody fragment", "humanized anti-Sema3A antibody fragment", "variant humanized anti-Sema3A antibody fragment" refer to a portion of a full length anti-Sema3A antibody, in which a variable region or a functional capability is retained, for example specific Sema3A epitope binding. Examples of antibody fragments include, but are not limited to, a Fab, Fab', F(ab')2, Fd, Fv, scFv and scFv-Fc fragment, a diabody, a linear antibody, a single-chain antibody, a minibody, a diabody formed from antibody fragments, and multispecific antibodies formed from antibody fragments.

Full length antibodies can be treated with enzymes such as papain or pepsin to generate useful antibody fragments. Papain digestion is used to produce two identical antigen-binding antibody fragments called "Fab" fragments, each with a single antigen-binding site, and a residual "Fc" fragment. The Fab fragment also contains the constant domain of the light chain and the $C_{H1}$ domain of the heavy chain. Pepsin treatment yields a F(ab')$_2$ fragment that has two antigen-binding sites and is still capable of cross-linking antigen.

Fab' fragments differ from Fab fragments by the presence of additional residues including one or more cysteines from the antibody hinge region at the C-terminus of the $C_{H1}$ domain. F(ab')$_2$ antibody fragments are pairs of Fab' fragments linked by cysteine residues in the hinge region. Other chemical couplings of antibody fragments are also known.

"Fv" fragment contains a complete antigen-recognition and binding site consisting of a dimer of one heavy and one light chain variable domain in tight, non-covalent association. In this configuration, the three CDRs of each variable domain interact to define an antigen-biding site on the surface of the $V_H$-$V_L$ dimer. Collectively, the six CDRs confer antigen-binding specificity to the antibody.

A "single-chain Fv" or "scFv" antibody fragment is a single chain Fv variant comprising the $V_H$ and $V_L$ domains of an antibody where the domains are present in a single polypeptide chain. The single chain Fv is capable of recognizing and binding antigen. The scFv polypeptide may optionally also contain a polypeptide linker positioned between the $V_H$ and $V_L$ domains in order to facilitate formation of a desired three-dimensional structure for antigen binding by the scFv (see, e.g., Pluckthun, 1994, In The Pharmacology of monoclonal Antibodies, Vol. 113, Rosenburg and Moore eds., Springer-Verlag, New York, pp. 269-315).

Other recognized antibody fragments include those that comprise a pair of tandem Fd segments ($V_H$-$C_{H1}$-$V_H$-$C_{H1}$) to form a pair of antigen binding regions. These "linear antibodies" can be bispecific or monospecific as described in, for example, Zapata et al. 1995, Protein Eng. 8(10):1057-1062.

A humanized antibody or a humanized antibody fragment is a specific type of chimeric antibody which includes an immunoglobulin amino acid sequence variant, or fragment thereof, which is capable of binding to a predetermined antigen and which, comprises one or more FRs having substantially the amino acid sequence of a human immunoglobulin and one or more CDRs having substantially the amino acid sequence of a non-human immunoglobulin. This non-human amino acid sequence often referred to as an "import" sequence is typically taken from an "import" antibody domain, particularly a variable domain. In general, a humanized antibody includes at least the CDRs or HVLs of a non-human antibody, inserted between the FRs of a human heavy or light chain variable domain.

The present invention describes specific humanized anti-Sema3A antibodies which contain CDRs derived from a murine or chimeric antibody inserted between the FRs of human germline sequence heavy and light chain variable domains. It will be understood that certain murine FR residues may be important to the function of the humanized antibodies and therefore certain of the human germline sequence heavy and light chain variable domains residues are modified to be the same as those of the corresponding murine sequence.

As used herein, the expressions "antibody of the invention" and the "anti-Sema3A antibody of the invention" refer to the anti-Sema3A antibody or an antigen-binding fragment thereof described herein. Preferably, said expressions refer to any antibody comprising a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3), and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In one aspect, a humanized anti-Sema3A antibody comprises substantially all of at least one, and typically two, variable domains (such as contained, for example, in Fab, Fab', F(ab')2, Fabc, and Fv fragments) in which all, or substantially all, of the CDRs correspond to those of a non-human immunoglobulin, and specifically herein, the CDRs are murine sequences, and the FRs are those of a human immunoglobulin consensus or germline sequence. In another aspect, a humanized anti-Sema3A antibody also includes at least a portion of an immunoglobulin Fc region, typically that of a human immunoglobulin. Ordinarily, the antibody will contain both the light chain as well as at least the variable domain of a heavy chain. The antibody also may include one or more of the $C_{H1}$, hinge, $C_{H2}$, $C_{H3}$, and/or $C_{H4}$ regions of the heavy chain, as appropriate.

A humanized anti-Sema3A antibody can be selected from any class of immunoglobulins, including IgM, IgG, IgD, IgA and IgE, and any isotype, including IgG$_1$, IgG$_2$, IgG$_3$, IgG$_4$, IgA$_1$ and IgA$_2$. For example, the constant domain can be a complement fixing constant domain where it is desired that the humanized antibody exhibit cytotoxic activity, and the isotype is typically IgG$_1$. Where such cytotoxic activity is not desirable, the constant domain may be of another isotype, e.g., IgG$_2$. An alternative humanized anti-Sema3A antibody can comprise sequences from more than one immunoglobulin class or isotype, and selecting particular constant domains to optimize desired effector functions is within the ordinary skill in the art. In specific embodiments, the present invention provides antibodies that are IgG1 antibodies and more particularly IgG1 antibodies characterized by a reduced effector function.

Preferably, the anti-Sema3A antibody of the invention is a humanized antibody formatted as IgG1 KO.

The FRs and CDRs, or HVLs, of a humanized anti-Sema3A antibody do need not to correspond precisely to the parental sequences. For example, one or more residues in the import CDR, or HVL, or the consensus or germline FR sequence may be altered (e.g., mutagenized) by substitution, insertion or deletion such that the resulting amino acid residue is no longer identical to the original residue in the corresponding position in either parental sequence but the antibody nevertheless retains the function of binding to Sema3A. Such alteration typically will not be extensive and will be conservative alterations. Usually, at least 75% of the humanized antibody residues will correspond to those of the parental consensus or germline FR and import CDR sequences, more often at least 90%, and most frequently greater than 95%, or greater than 98% or greater than 99%.

Immunoglobulin residues that affect the interface between heavy and light chain variable regions ("the $V_L$-$V_H$ interface") are those that affect the proximity or orientation of the two chains with respect to one another. Certain residues that may be involved in interchain interactions include $V_L$ residues 34, 36, 38, 44, 46, 87, 89, 91, 96, and 98 and $V_H$ residues 35, 37, 39, 45, 47, 91, 93, 95, 100, and 103 (utilizing the numbering system set forth in Kabat et al., Sequences of Proteins of Immunological Interest (National Institutes of Health, Bethesda, Md., 1987)). U.S. Pat. No. 6,407,213 also discusses that residues such as $V_L$ residues 43 and 85, and $V_H$ residues 43 and 60 also may be involved in this interaction. While these residues are indicated for human IgG only, they are applicable across species. Important antibody residues that are reasonably expected to be involved in interchain interactions are selected for substitution into the consensus sequence.

The terms "consensus sequence" and "consensus antibody" refer to an amino acid sequence which comprises the most frequently occurring amino acid residue at each location in all immunoglobulins of any particular class, isotype, or subunit structure, e.g., a human immunoglobulin variable domain. The consensus sequence may be based on immunoglobulins of a particular species or of many species. A "consensus" sequence, structure, or antibody is understood to encompass a consensus human sequence as described in certain embodiments, and to refer to an amino acid sequence which comprises the most frequently occurring amino acid residues at each location in all human immunoglobulins of any particular class, isotype, or subunit structure. Thus, the consensus sequence contains an amino acid sequence having at each position an amino acid that is present in one or more known immunoglobulins, but which may not exactly duplicate the entire amino acid sequence of any single immunoglobulin. The variable region consensus sequence is not obtained from any naturally produced antibody or immunoglobulin. Kabat et al., 1991, Sequences of Proteins of Immunological Interest, 5th Ed. Public Health Service, National Institutes of Health, Bethesda, Md., and variants thereof. The FRs of heavy and light chain consensus sequences, and variants thereof, provide useful sequences for the preparation of humanized anti-Sema3A antibodies. See, for example, U.S. Pat. Nos. 6,037,454 and 6,054,297.

Human germline sequences are found naturally in human population. A combination of those germline genes generates antibody diversity. Germline antibody sequences for the light chain of the antibody come from conserved human germline kappa or lambda v-genes and j-genes. Similarly, the heavy chain sequences come from germline v-, d- and j-genes (LeFranc, M-P, and LeFranc, G, "The Immunoglobulin Facts Book" Academic Press, 2001).

An "isolated" antibody is one that has been identified and separated and/or recovered from a component of its natural environment. Contaminant components of the antibody's natural environment are those materials that may interfere with diagnostic or therapeutic uses of the antibody, and can be enzymes, hormones, or other proteinaceous or nonproteinaceous solutes. In one aspect, the antibody will be purified to at least greater than 95% isolation by weight of antibody.

The term "antibody performance" refers to factors/properties that contribute to antibody recognition of antigen or the effectiveness of an antibody in vivo. In a preferred embodiment, it refers to the ability of the antibody to prevent cytoskeletal collapse in retinal cells. Changes in the amino acid sequence of an antibody can affect antibody properties such as folding, and can influence physical factors such as initial rate of antibody binding to antigen ($k_a$), dissociation constant of the antibody from antigen ($k_d$), affinity constant of the antibody for the antigen (Kd), conformation of the antibody, protein stability, and half-life of the antibody.

As used herein, the terms "identical" or "percent identity," in the context of two or more nucleic acids or polypeptide sequences, refer to two or more sequences or subsequences that are the same or have a specified percentage of nucleotides or amino acid residues that are the same, when compared and aligned for maximum correspondence. To determine the percent identity, the sequences are aligned for optimal comparison purposes (e.g., gaps can be introduced in the sequence of a first amino acid or nucleic acid sequence for optimal alignment with a second amino or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=# of identical positions/total # of positions (e.g., overlapping positions)×100). In some embodiments, the two sequences that are compared are the same length after gaps are introduced within the sequences, as appropriate (e.g., excluding additional sequence extending beyond the sequences being compared). For example, when variable region sequences are compared, the leader and/or constant domain sequences are not considered. For sequence comparisons between two sequences, a "corresponding" CDR refers to a CDR in the same location in both sequences (e.g., CDR-H1 of each sequence).

The determination of percent identity or percent similarity between two sequences can be accomplished using a mathematical algorithm. A preferred, non-limiting example of a mathematical algorithm utilized for the comparison of two sequences is the algorithm of Karlin and Altschul, 1990, Proc. Natl. Acad. Sci. USA 87:2264-2268, modified as in Karlin and Altschul, 1993, Proc. Natl. Acad. Sci. USA 90:5873-5877. Such an algorithm is incorporated into the NBLAST and XBLAST programs of Altschul et al., 1990, J. Mol. Biol. 215:403-410. BLAST nucleotide searches can be performed with the NBLAST program, score=100, wordlength=12, to obtain nucleotide sequences homologous to a nucleic acid encoding a protein of interest. BLAST protein searches can be performed with the XBLAST program, score=50, wordlength=3, to obtain amino acid sequences homologous to protein of interest. To obtain gapped alignments for comparison purposes, Gapped BLAST can be utilized as described in Altschul et al., 1997, Nucleic Acids Res. 25:3389-3402. Alternatively, PSI-Blast can be used to perform an iterated search which detects distant relationships between molecules (Id.). When utilizing BLAST, Gapped BLAST, and PSI-Blast programs, the default parameters of the respective programs (e.g., XBLAST and NBLAST) can be used. Another preferred, non-limiting example of a mathematical algorithm utilized for the comparison of sequences is the algorithm of Myers and Miller, CABIOS (1989). Such an algorithm is incorporated into the ALIGN program (version 2.0) which is part of the GCG sequence alignment software package. When utilizing the ALIGN program for comparing amino acid sequences, a PAM120 weight residue table, a gap length penalty of 12, and a gap penalty of 4 can be used. Additional algorithms for sequence analysis are known in the art and include ADVANCE and ADAM as described in Torellis and Robotti, 1994, Comput. Appl. Biosci. 10:3-5; and FASTA described in Pearson and Lipman, 1988, Proc. Natl. Acad. Sci. USA 85:2444-8. Within FASTA, ktup is a control option that sets the sensitivity and speed of the search. If ktup=2, similar regions in the two sequences being compared are found by looking at pairs of aligned residues; if ktup=1, single aligned amino acids are examined. ktup can be set to 2 or 1 for protein sequences, or from 1 to 6 for DNA sequences. The default if ktup is not specified is 2 for proteins and 6 for DNA. Alternatively, protein sequence alignment may be carried out using the CLUSTAL W algorithm, as described by Higgins et al., 1996, Methods Enzymol. 266:383-402.

As used herein, the expressions "cell", "cell line", and "cell culture" are used interchangeably and all such designations include the progeny thereof. Thus, "transformants" and "transformed cells" include the primary subject cell and cultures derived therefrom without regard for the number of transfers.

The term "mammal" for purposes of treatment refers to any animal classified as a mammal, including humans, domesticated and farm animals, and zoo, sports, or pet animals, such as dogs, horses, cats, cows, and the like. Preferably, the mammal is human.

A "disease" or "disorder", as used herein, is any condition that would benefit from treatment with a humanized anti-Sema3A antibody described herein. This includes chronic and acute disorders or diseases including those pathological conditions that predispose the mammal to the disorder in question.

The term "intravitreal injection" has its normal meaning in the art and refers to introduction of an anti-Sema3A antibody or an antigen-binding fragment thereof into the vitreous of a patient.

The term "subcutaneous administration" refers to introduction of an anti-Sema3A antibody or an antigen-binding fragment thereof under the skin of an animal or human patient, preferable within a pocket between the skin and underlying tissue, by relatively slow, sustained delivery from a drug receptacle. Pinching or drawing the skin up and away from underlying tissue may create the pocket.

The term "subcutaneous infusion" refers to introduction of a drug under the skin of an animal or human patient, preferably within a pocket between the skin and underlying tissue, by relatively slow, sustained delivery from a drug receptacle for a period of time including, but not limited to, 30 minutes or less, or 90 minutes or less. Optionally, the infusion may be made by subcutaneous implantation of a drug delivery pump implanted under the skin of the animal or human patient, wherein the pump delivers a predetermined amount of drug for a predetermined period of time, such as 30 minutes, 90 minutes, or a time period spanning the length of the treatment regimen.

The term "subcutaneous bolus" refers to drug administration beneath the skin of an animal or human patient, where bolus drug delivery is less than approximately 15 minutes, in another aspect, less than 5 minutes, and in still another aspect, less than 60 seconds. In yet another aspect, administration is within a pocket between the skin and underlying tissue, where the pocket may be created by pinching or drawing the skin up and away from underlying tissue.

The term "therapeutically effective amount" is used to refer to an amount of an anti-Sema3A antibody or an antigen-binding fragment thereof that relieves or ameliorates one or more of the symptoms of the disorders being treated. In doing so it is that amount that has a beneficial patient outcome. Efficacy can be measured in conventional ways, depending on the condition to be treated. For example, in eye/retinal diseases or disorders characterized by cells expressing Sema3A, efficacy can be measured by determining the response rates, e.g. restoration of vision or by assessing the time of delay until disease progression.

The terms "treatment" and "therapy" and the like, as used herein, are meant to include therapeutic as well as prophylactic, or suppressive measures for a disease or disorder leading to any clinically desirable or beneficial effect, including but not limited to alleviation or relief of one or more symptoms, regression, slowing or cessation of progression of the disease or disorder. Thus, for example, the term treatment includes the administration of an anti-Sema3A antibody or an antigen-binding fragment thereof prior to or following the onset of a symptom of a disease or disorder thereby preventing or removing one or more signs of the disease or disorder. As another example, the term includes the administration of an anti-Sema3A antibody or an antigen-binding fragment thereof after clinical manifestation of the disease to combat the symptoms of the disease. Further, administration of an anti-Sema3A antibody or an antigen-binding fragment thereof after onset and after clinical symptoms have developed where administration affects clinical parameters of the disease or disorder, whether or not the treatment leads to amelioration of the disease, comprises "treatment" or "therapy" as used herein. Moreover, as long as the compositions of the invention either alone or in combination with another therapeutic agent alleviate or ameliorate at least one symptom of a disorder being treated as compared to that symptom in the absence of use of the anti-Sema3A antibody composition or an antigen-binding fragment thereof, the result should be considered an effective treatment of the underlying disorder regardless of whether all the symptoms of the disorder are alleviated or not.

The term "package insert" is used to refer to instructions customarily included in commercial packages of therapeutic products, that contain information about the indications, usage, administration, contraindications and/or warnings concerning the use of such therapeutic products.

Antibody of the Invention

In a first aspect, the invention relates to an anti-Sema3A antibody or an antigen-binding fragment thereof. Preferably, said antibody is a humanized anti-Sema3A antibody, more preferably a humanized monoclonal anti-Sema3A antibody.

In an initial characterization, a library of antibodies targeting Sema3A variants was generated by placing the CDRs of murine antibodies into FRs of the human consensus heavy and light chain variable domains and furthermore by engineering the FRs with different alterations.

This resulted in a humanized antibody directed against Sema3A with enhanced properties as disclosed herein. The sequences of the antibody of the invention are shown in the table 1 below.

TABLE 1

| Name | Amino acid sequence | SEQ ID NO |
|---|---|---|
| HCDR1 | SYYMS | SEQ ID NO: 1 |
| HCDR2 | TIIKSGGYAY YPDSVKD | SEQ ID NO: 2 |

TABLE 1-continued

| Name | Amino acid sequence | SEQ ID NO |
| --- | --- | --- |
| HCDR3 | GGQGAMDY | SEQ ID NO: 3 |
| LCDR1 | RASQSIGDYLH | SEQ ID NO: 4 |
| LCDR2 | YASQSIS | SEQ ID NO: 5 |
| LCDR3 | QQGYSFPYT | SEQ ID NO: 6 |
| VH - variant 1 | EVQLVESGGG LVQPGGSLRL SCAASGFTFS SYYMSWVRQA PGKGLEWVST IIKSGGYAYY PDSVKDRFTI SRDNSKNTLY LQMSSLRAED TAVYYCVRGG QGAMDYWGQG TTVTVSS | SEQ ID NO: 7 |
| VH - variant 2 | EVQLVESGGG LVQPGGSLRL SCAASGFPFS SYYMSWVRQA PGKGLEWVST IIKSGGYAYY PDSVKDRFTI SRDNSKNTLY LQMSSLRAED TAVYYCVRGG QGAMDYWGQG TTVTVSS | SEQ ID NO: 8 |
| VH - variant 3 | EVQLVESGGG LVQLGGSLRL SCAASGFTFS SYYMSWVRQA PGKGLEWVST IIKSGGYAYY PDSVKDRFTI SRDNSKNTLY LQMNSLRAED TAVYYCVKGG QGAMDYWGQG TTVTVSS | SEQ ID NO: 9 |
| VH - variant 4 | EVQLVESGGG LLQLGGSLRL SCAASGFTFS SYYMSWVRQA PGKGLEWVST IIKSGGYAYY PDSVKDRFTI SRDNSKNTLN LQMNSLRAED TAVYYCVKGG QGAMDYWGQG TTVTVSS | SEQ ID NO: 10 |
| VL - variant a | EIVLTQSPAT LSLSPGERAT LSCRASQSIG DYLHWYQQKP GQAPRLLIKY ASQSISGIPA RFSGSGSGTD FTLTITSLEP EDFAVYYCQQ GYSFPYTFGG GTKLEIK | SEQ ID NO: 11 |
| VL - variant b | EIVLTQSPAT LSLSPGERAT LSCRASQSIG DYLHWYQQKP GQAPRLLIYY ASQSISGIPA RFSGSGSGTD FTLTISSLEP EDFAVYYCQQ GYSFPYTFGG GTKLEIK | SEQ ID NO: 12 |
| VL - variant c | EIVLTQSPAT LSLSPGERAT LSCRASQSIG DYLHWYQQKP GQAPRLLIKY ASQSISGIPA RFSGSGSGTD FTLTISSLEP EDFAVYYCQQ GYSFPYTFGG GTKLEIK | SEQ ID NO: 13 |
| Heavy Chain- Clone I | EVQLVESGGG LVQPGGSLRL SCAASGFTFS SYYMSWVRQA PGKGLEWVST IIKSGGYAYY PDSVKDRFTI SRDNSKNTLY LQMSSLRAED TAVYYCVRGG QGAMDYWGQG TTVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA PIEKTISKAK GQPREPQVYT LPPSREEMTK NQVSLTCLVK GFYPSDIAVE WESNGQPENN YKTTPPVLDS DGSFFLYSKL TVDKSRWQQG NVFSCSVMHE ALHNHYTQKS LSLSPG | SEQ ID NO: 14 |
| Light Chain- Clone I | EIVLTQSPAT LSLSPGERAT LSCRASQSIG DYLHWYQQKP GQAPRLLIKY ASQSISGIPA RFSGSGSGTD FTLTITSLEP EDFAVYYCQQ GYSFPYTFGG GTKLEIKRTV AAPSVFIFPP SDEQLKSGTA SVVCLLNNFY PREAKVQWKV DNALQSGNSQ ESVTEQDSKD STYSLSSTLT LSKADYEKHK VYACEVTHQG LSSPVTKSFN RGEC | SEQ ID NO: 15 |
| Heavy Chain- Clone II | EVQLVESGGG LVQPGGSLRL SCAASGFPFS SYYMSWVRQA PGKGLEWVST IIKSGGYAYY PDSVKDRFTI SRDNSKNTLY LQMSSLRAED TAVYYCVRGG QGAMDYWGQG TTVTVSSAST KGPSVFPLAP SSKSTSGGTA ALGCLVKDYF PEPVTVSWNS GALTSGVHTF PAVLQSSGLY SLSSVVTVPS SSLGTQTYIC NVNHKPSNTK VDKRVEPKSC DKTHTCPPCP APEAAGGPSV FLFPPKPKDT LMISRTPEVT CVVVDVSHED PEVKFNWYVD GVEVHNAKTK PREEQYNSTY RVVSVLTVLH QDWLNGKEYK CKVSNKALPA | SEQ ID NO: 16 |

TABLE 1-continued

| Name | Amino acid sequence | SEQ ID NO |
|---|---|---|
| | PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPG | |
| Heavy<br>Chain-<br>Clone III | EVQLVESGGG LVQLGGSLRL SCAASGFTFS<br>SYYMSWVRQA PGKGLEWVST IIKSGGYAYY<br>PDSVKDRFTI SRDNSKNTLY LQMNSLRAED<br>TAVYYCVKGG QGAMDYWGQG TTVTVSSAST<br>KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKRVEPKSC DKTHTCPPCP APEAAGGPSV<br>FLFPPKPKDT LMISRTPEVT CVVVDVSHED<br>PEVKFNWYVD GVEVHNAKTK PREEQYNSTY<br>RVVSVLTVLH QDWLNGKEYK CKVSNKALPA<br>PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPG | SEQ ID NO: 17 |
| Light<br>Chain-<br>Clone III | EIVLTQSPAT LSLSPGERAT LSCRASQSIG<br>DYLHWYQQKP GQAPRLLIYY ASQSISGIPA<br>RFSGSGSGTD FTLTISSLEP EDFAVYYCQQ<br>GYSFPYTFGG GTKLEIKRTV AAPSVFIFPP<br>SDEQLKSGTA SVVCLLNNFY PREAKVQWKV<br>DNALQSGNSQ ESVTEQDSKD STYSLSSTLT<br>LSKADYEKHK VYACEVTHQG LSSPVTKSFN RGEC | SEQ ID NO: 18 |
| Heavy<br>Chain-<br>Clone IV | EVQLVESGGG LLQLGGSLRL SCAASGFTFS<br>SYYMSWVRQA PGKGLEWVST IIKSGGYAYY<br>PDSVKDRFTI SRDNSKNTLN LQMNSLRAED<br>TAVYYCVKGG QGAMDYWGQG TTVTVSSAST<br>KGPSVFPLAP SSKSTSGGTA ALGCLVKDYF<br>PEPVTVSWNS GALTSGVHTF PAVLQSSGLY<br>SLSSVVTVPS SSLGTQTYIC NVNHKPSNTK<br>VDKRVEPKSC DKTHTCPPCP APEAAGGPSV<br>FLFPPKPKDT LMISRTPEVT CVVVDVSHED<br>PEVKFNWYVD GVEVHNAKTK PREEQYNSTY<br>RVVSVLTVLH QDWLNGKEYK CKVSNKALPA<br>PIEKTISKAK GQPREPQVYT LPPSREEMTK<br>NQVSLTCLVK GFYPSDIAVE WESNGQPENN<br>YKTTPPVLDS DGSFFLYSKL TVDKSRWQQG<br>NVFSCSVMHE ALHNHYTQKS LSLSPG | SEQ ID NO: 19 |
| Light<br>Chain-<br>Clone IV | EIVLTQSPAT LSLSPGERAT LSCRASQSIG<br>DYLHWYQQKP GQAPRLLIKY ASQSISGIPA<br>RFSGSGSGTD FTLTISSLEP EDFAVYYCQQ<br>GYSFPYTFGG GTKLEIKRTV AAPSVFIFPP<br>SDEQLKSGTA SVVCLLNNFY PREAKVQWKV<br>DNALQSGNSQ ESVTEQDSKD STYSLSSTLT<br>LSKADYEKHK VYACEVTHQG LSSPVTKSFN RGEC | SEQ ID NO: 20 |

In one embodiment, the present invention provides an anti-Sema3A antibody or an antigen-binding fragment thereof comprising:
a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In another embodiment, the present invention provides an anti-Sema3A antibody or an antigen-binding fragment thereof comprising:
a heavy chain variable region comprising an amino acid sequence at least 80%, at least 90%, at least 95%, at least 98%, or at least 99% identical to the amino acid sequence SEQ ID NO: 7, SEQ ID NO: 8, SEQ ID NO: 9 or SEQ ID NO: 10; and
a light chain variable region comprising an amino acid sequence at least 80%, at least 90%, at least 95%, at least 98%, or at least 99% identical to the amino acid sequence of SEQ ID NO: 11, SEQ ID NO: 12 or SEQ ID NO: 13.

In another embodiment, the present invention provides an anti-Sema3A antibody or an antigen-binding fragment thereof comprising:
a heavy chain variable region comprising an amino acid sequence at least 80%, at least 90%, at least 95%, at least 98%, or at least 99% identical to the amino acid sequence SEQ ID NO: 7, SEQ ID NO: 8, SEQ ID NO: 9 or SEQ ID NO: 10; and
a light chain variable region comprising an amino acid sequence at least 80%, at least 90%, at least 95%, at least 98%, or at least 99% identical to the amino acid sequence of SEQ ID NO: 11, SEQ ID NO: 12 or SEQ ID NO: 13;

wherein:
the heavy chain variable region comprises the amino acid sequence of SEQ ID NO: 1 (H-CDR1); the amino acid sequence of SEQ ID NO: 2 (H-CDR2); and the amino acid sequence of SEQ ID NO: 3 (H-CDR3); and
the light chain variable region comprises the amino acid sequence of SEQ ID NO: 4 (L-CDR1); the amino acid sequence of SEQ ID NO: 5 (L-CDR2); and the amino acid sequence of SEQ ID NO: 6 (L-CDR3).

In yet another embodiment, the present invention provides an anti-Sema3A antibody or an antigen-binding fragment thereof comprising:
a heavy chain variable region comprising the amino acid sequences of SEQ ID NO: 7, SEQ ID NO: 8, SEQ ID NO: 9 or SEQ ID NO: 10; and
a light chain variable region comprising the amino acid sequence of SEQ ID NO: 11, SEQ ID NO: 12 or SEQ ID NO: 13.

In a preferred embodiment, the invention provides an anti-Sema3A antibody or an antigen-binding fragment thereof comprising:
a variable heavy chain and a variable light chain comprising the amino acid sequences of SEQ ID NO: 7 and SEQ ID NO: 11, respectively;
a variable heavy chain and a variable light chain comprising the amino acid sequences of SEQ ID NO: 8 and SEQ ID NO: 11, respectively;
a variable heavy chain and a variable light chain comprising the amino acid sequences of SEQ ID NO: 9 and SEQ ID NO: 12, respectively; or
a variable heavy chain and a variable light chain comprising the amino acid sequences of SEQ ID NO: 10 and SEQ ID NO: 13, respectively.

In yet another embodiment, the present invention provides an anti-Sema3A antibody or an antigen-binding fragment thereof comprising:
a heavy chain comprising, preferably consisting of, the amino acid sequence of SEQ ID NO: 14, SEQ ID NO: 16, SEQ ID NO: 17 or SEQ ID NO: 19; and
a light chain comprising, preferably consisting of, the amino acid sequence of SEQ ID NO: 15, SEQ ID NO: 18 or SEQ ID NO: 20.

In a particular embodiment, the invention relates to an anti-Sema3A antibody or an antigen-binding fragment thereof comprising:
a. a heavy chain comprising the amino acid sequence of SEQ ID NO: 14 and a light chain comprising the amino acid sequence of SEQ ID NO: 15, said antibody being referred to as "clone I";
b. a heavy chain comprising the amino acid sequence of SEQ ID NO: 16 and a light chain comprising the amino acid sequence of SEQ ID NO: 15, said antibody being referred to as "clone II";
c. a heavy chain comprising the amino acid sequence of SEQ ID NO: 17 and a light chain comprising the amino acid sequence of SEQ ID NO: 18, said antibody being referred to as "clone III"; or
d. a heavy chain comprising the amino acid sequence of SEQ ID NO: 19 and a light chain comprising the amino acid sequence of SEQ ID NO: 20, said antibody being referred to as "clone IV".

IgG1-KO mutants have been made by introducing mutations in the Fc region. Mutations to reduce or inhibit effector function are well known by the skilled person and thoroughly disclosed in prior art, for example in Wang et al, Protein Cell 2018, 9(1):63-73 and Stewart et al. Journal for ImmunoTherapy of Cancer 2014, 2:29. Typically, a non limiting list of mutations introduced in the IgG1 Fc region in order to reduce the effector function of the Fc comprises:
L234A and L235A;
L234A, L235A, and N297Q;
L234A, L235A, and P329G; or
L234A, L235A, and D265A;
wherein the residues are numbered according to the EU index of Kabat.

In a preferred embodiment, the antibody of the invention comprises the two mutations L234A and L235A in the Fc region to reduce effector function.

The CDR disclosed herein and depicted in SEQ ID NO: 1 to 6 are presented according to the Kabat numbering and are summarized in table 2 below with the Kabat position.

TABLE 2

| CDR | Kabat Sequence | Kabat position | SEQ ID NO: |
|---|---|---|---|
| HCDR1 | SYYMS | 31-35 | 1 |
| HCDR2 | TIIKSGGYAYYPDSVKD | 50-66 | 2 |
| HCDR3 | GGQGAMDY | 99-106 | 3 |
| LCDR1 | RASQSIGDYLH | 24-34 | 4 |
| LCDR2 | YASQSIS | 50-56 | 5 |
| LCDR3 | QQGYSFPYT | 89-97 | 6 |

The anti-Sema3A antibody of the present invention binds with high affinity to human Sema3A. In an embodiment relating to this aspect, an anti-Sema3A antibody of the present invention binds to human Sema3A at a $K_D$<50 pM. In another embodiment, the anti-Sema3A antibody of the present invention binds to human Sema3A at a $K_D$<35 pM, as exemplified in example 4. In a preferred embodiment, the anti-Sema3A antibody of the present invention binds to human Sema3A at a $K_D$<30 pM.

The anti-Sema3A antibody of the invention also binds to cyno-Sema3A, mouse Sema3A, rat Sema3A and rabbit Sema3A.

The anti-Sema3A antibody of the present invention prevents Sema3A-induced cytoskeletal collapse in retinal cells with a functional potency of less than 100 pM, preferably less than 80 pM, more preferably less than 70 pM. In a preferred embodiment, the anti-Sema3A antibody of the present invention prevents Sema3A-induced cytoskeletal collapse in retinal cells with a functional potency of 69 pM, as exemplified in example 4.

In a further aspect, the anti-Sema3A antibody of the present invention proved to have a low immunogenicity risk as described in example 5. This relies on an in silico prediction of the immunogenicity of the antibody. The immunogenicity risk is typically assessed by various methods well known such as by computer algorithm for predicting T cell epitopes, a major immunogenicity-influencing factor.

It has been indeed reported that sequences containing T-cell epitopes present in proteins of interest could be predicted by using an algorithm based on a computational matrix approach, available under the name EpiMatrix (produced by EpiVax). The person skilled in the art may refer to Van Walle et al., Expert Opin Biol Ther. 2007 March; 7(3): 405-18 and Jawa and al., Clin Immunol. 2013 December; 149(3):534-55.

The inventors have shown that the antibody of the invention shows more advantageous properties than other antibodies or fragments targeting Sema3A mentioned in prior art and described herein.

The inventors have compared the binding affinity of an antibody targeting Sema3A disclosed in WO2014123186 (Chiome Bioscience) with the affinity of the antibody of the present invention. The antibodies of WO2014123186 are disclosed for use in the treatment of Alzheimer's disease. The present example 8 shows that the antibody of the invention proved to have higher binding affinities for human Sema3A than the prior art antibody disclosed by Chiome Bioscience.

The inventors have also compared the properties of the antibody in accordance with the present invention with the ScFv fragments as disclosed in WO2017074013 (Samsung). These fragments are disclosed for use in treatment of various cancers. The example 9 shows that the antibody of the invention proved to have higher binding affinities for human Sema3A than the prior art antibody fragments disclosed by WO2017074013.

A higher binding affinity prolongs the time for neutralization of Sema3A after intravitreal injection of the antibody and allows a reduced injection frequency. A higher binding affinity further allows the administration of a lower dose, limiting the potential side effects. The antibody of the invention thus provides technical advantages over the prior art antibodies. The improved binding affinity and reduced injection frequency considerably ameliorate the efficacy of the treatment of patients in need thereof. It also provides valuable benefits for the patient, especially an improved drug observance and compliance.

The inventors have also compared the functional potency of the antibody of the invention and a commercially available antibody targeting Sema3A as described in Example 11. The inventors have shown that, under the same conditions, the antibody of the invention prevents Sema3A-induced cytoskeletal collapse in retinal cells (Example 3), whereas the commercially available antibody does not (Example 11).

Humanization and Amino Acid Sequence Variants

Further variant anti-Sema3A antibodies and antibody fragments can be engineered based on the set of CDRs identified under the sequences depicted in SEQ ID NO: 1 to 6. It is to be understood that in said variant anti-Sema3A antibodies and antibody fragments the amino acid sequence of the CDRs remain unchanged but the surrounding regions e.g. FR regions can be engineered. Amino acid sequence variants of the anti-Sema3A antibody can be prepared by introducing appropriate nucleotide changes into the anti-Sema3A antibody DNA, or by peptide synthesis. Such variants include, for example, deletions from, and/or insertions into and/or substitutions of, residues within the amino acid sequences of the anti-Sema3A antibodies of the examples herein. Any combination of deletions, insertions, and substitutions is made to arrive at the final construct, provided that the final construct possesses the desired characteristics. The amino acid changes also may alter post-translational processes of the humanized or variant anti-Sema3A antibody, such as changing the number or position of glycosylation sites.

Another type of amino acid variant of the antibody involves altering the original glycosylation pattern of the antibody. The term "altering" in this context means deleting one or more carbohydrate moieties found in the antibody, and/or adding one or more glycosylation sites that were not previously present in the antibody.

In some aspects, the present invention includes nucleic acid molecules that encode the amino acid sequence variants of the anti-Sema3A antibodies described herein. Nucleic acid molecules encoding amino acid sequence variants of the anti-Sema3A antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the anti-Sema3A antibody.

In certain embodiments, the anti-Sema3A antibody is an antibody fragment. There are techniques that have been developed for the production of antibody fragments. Fragments can be derived via proteolytic digestion of intact antibodies (see, e.g., Morimoto et al., 1992, Journal of Biochemical and Biophysical Methods 24:107-117; and Brennan et al., 1985, Science 229:81). Alternatively, the fragments can be produced directly in recombinant host cells. For example, Fab'-SH fragments can be directly recovered from $E.$ $coli$ and chemically coupled to form $F(ab')_2$ fragments (see, e.g., Carter et al., 1992, Bio/Technology 10:163-167). By another approach, $F(ab')_2$ fragments can be isolated directly from recombinant host cell culture. Other techniques for the production of antibody fragments will be apparent to the skilled practitioner.

The anti-Sema3A antibodies and antigen-binding fragments thereof can include modifications.

In certain embodiments, it may be desirable to use an anti-Sema3A antibody fragment, rather than an intact antibody. It may be desirable to modify the antibody fragment in order to increase its serum half-life. This can be achieved, for example, by incorporation of a salvage receptor binding epitope into the antibody fragment. In one method, the appropriate region of the antibody fragment can be altered (e.g., mutated), or the epitope can be incorporated into a peptide tag that is then fused to the antibody fragment at either end or in the middle, for example, by DNA or peptide synthesis. See, e.g., WO 96/32478.

In other embodiments, the present invention includes covalent modifications of the anti-Sema3A antibodies. Covalent modifications include modification of cysteinyl residues, histidyl residues, lysinyl and amino-terminal residues, arginyl residues, tyrosyl residues, carboxyl side groups (aspartyl or glutamyl), glutaminyl and asparaginyl residues, or seryl, or threonyl residues. Another type of covalent modification involves chemically or enzymatically coupling glycosides to the antibody. Such modifications may be made by chemical synthesis or by enzymatic or chemical cleavage of the antibody, if applicable. Other types of covalent modifications of the antibody can be introduced into the molecule by reacting targeted amino acid residues of the antibody with an organic derivatizing agent that is capable of reacting with selected side chains or the amino- or carboxy-terminal residues.

Removal of any carbohydrate moieties present on the antibody can be accomplished chemically or enzymatically. Chemical deglycosylation is described by Hakimuddin et al., 1987, Arch. Biochem. Biophys. 259:52 and by Edge et al., 1981, Anal. Biochem., 118:131. Enzymatic cleavage of carbohydrate moieties on antibodies can be achieved by the use of a variety of endo- and exo-glycosidases as described by Thotakura et al., 1987, Meth. Enzymol 138:350.

Another type of useful covalent modification comprises linking the antibody to one of a variety of nonproteinaceous polymers, e.g., polyethylene glycol, polypropylene glycol, or polyoxyalkylenes, in the manner set forth in one or more of U.S. Pat. Nos. 4,640,835, 4,496,689, 4,301,144, 4,670,417, 4,791,192 and 4,179,337.

Epitope Binding

In a second aspect, the invention relates to an antibody that recognises a specific "Sema3A antigen epitope" and "Sema3A epitope". In particular, the antibody of the invention binds to an epitope of the human Sema3A with the SEQ ID NO: 22.

In one aspect, the invention relates to an anti-Sema3A antibody or an antigen-binding fragment thereof that binds to at least one amino acid residue within amino acid regions 370-382 of human Sema3A as set forth in SEQ ID NO: 22.

In another aspect, the invention relates to an anti-Sema3A antibody or an antigen-binding fragment thereof that binds to SEQ ID NO: 21.

The sequences SEQ ID NO: 21 and 22 are depicted in the table 5 below.

ceptor complex of the ligand Sema3A, the receptor Plexin A and the co-receptor Nrp1, leading to the interference with the biological effects of such signaling.

In the context of epitope binding, the phrase "binds within amino acid regions X-Y . . . " means that the anti-Sema3A antibody or an antigen-binding fragment thereof binds to at least one, preferably all of the, amino acid residue within the amino acid region specified in the sequence.

In another aspect, an anti-Sema3A antibody or an antigen-binding fragment thereof binds to at least 10%, 20%, 30%, 40%, 50%, 60%, 70%, 80%, 85%, 90%, 95%, or 100% of the amino acid sequence depicted in SEQ ID NO: 22. Preferably, an anti-Sema3A antibody or an antigen-binding fragment thereof binds to SEQ ID NO: 22.

Therapeutic Uses

In a third aspect, the invention relates to an anti-Sema3A antibody or an antigen-binding fragment thereof for use as a medicament.

TABLE 5

| Name | Sequence | SEQ ID NO: |
|---|---|---|
| Sema3A epitope | DSTKDLPDDVITF | 21 |
| Human Sema3A | NYQNGKNNVPRLKLSYKEMLESNNVITFNGLANSSSYHTFL LDEERSRLYVGAKDHIFSFDLVNIKDFQKIVWPVSYTRRDEC KWAGKDILKECANFIKVLKAYNQTHLYACGTGAFHPICTYIEI GHHPEDNIFKLENSHFENGRGKSPYDPKLLTASLLIDGELYS GTAADFMGRDFAIFRTLGHHHPIRTEQHDSRWLNDPKFISA HLISESDNPEDDKVYFFFRENAIDGEHSGKATHARIGQICKN DFGGHRSLVNKWTTFLKARLICSVPGPNGIDTHFDELQDVF LMNFKDPKNPVVYGVFTTSSNIFKGSAVCMYSMSDVRRVF LGPYAHRDGPNYQWVPYQGRVPYPRPGTCPSKTFGGFDS TKDLPDDVITFARSHPAMYNPVFPMNNRPIVIKTDVNYQFT QIVVDRVDAEDGQYDVMFIGTDVGTVLKVVSIPKETWYDLE EVLLEEMTVFREPTAISAMELSTKQQQLYIGSTAGVAQLPLH RCDIYGKACAECCLARDPYCAWDGSACSRYFPTAKRRTRR QDIRNGDPLTHCSDLHHDNHHGHSPEERIIYGVENSSTFLE CSPKSQRALVYWQFQRRNEERKEEIRVDDHIIRTDQGLLLR SLQQKDSGNYLCHAVEHGFIQTLLKVTLEVIDTEHLEELLHK DDDGDGSKTKEMSNSMTPSQKVWYRDFMQLINHPNLNTM DEFCEQVWKRDRKQRRQRPGHTPGNSNKWKHLQENKKG RNRRTHEFERAPRSV | 22 |

As used herein, the terms "Sema3A antigen epitope" and "Sema3A epitope" refer to a molecule (e.g., a peptide) or a fragment of a molecule capable of binding to an anti-Sema3A antibody or an antigen-binding fragment thereof. These terms further include, for example, a Sema3A antigenic determinant recognized by any of the antibodies or antibody fragments of the present invention, which has a light and heavy chain CDR combination selected from heavy chain CDRs of the SEQ ID NOs 1 to 3 and light chain CDRs of the SEQ ID NOs: 4 to 6.

Sema3A antigen epitopes can be included in proteins, protein fragments, peptides or the like. The epitopes are most commonly proteins, short oligopeptides, oligopeptide mimics (i.e., organic compounds that mimic antibody binding properties of the Sema3A antigen), or combinations thereof.

It has been found that the antibodies or antibody fragments of the present invention bind to a unique epitope of the human Sema3A. Preferably, an anti-Sema3A antibody or an antigen-binding fragment thereof binds to at least one amino acid residue within amino acid regions 370-382 of the extracellular domain of human Sema3A with the SEQ ID NO: 22. This epitope is located close to the interface of Sema3A and a Plexin A receptor. Binding of the antibody to this epitope inhibits the formation of the signaling holore- In one embodiment, the present invention provides an anti-Sema3A or an antigen-binding fragment for inhibiting the vasorepressive effect of SemaA, and/or for improving revascularisation of the retina.

Preferably, the present invention provides an anti-Sema3A antibody or an antigen-binding fragment thereof for use in the treatment or prevention of a retinal or eye disease. The inventors have indeed developed an antibody targeting Sema3A, which is extremely helpful for:
  redirecting angiogenesis towards ischemic regions, in order to improve revascularisation of the retina;
  preventing pathological neovascularization of the vitreous region; and
  preventing blood retinal barrier breakdown.

As previously mentioned, Sema3A is a vasorepulsive cue secreted by hypoxic retinal ganglion cells. By binding to neuropilin-1, it activates the intracellular signalling of plexin receptors on endothelial cells resulting in disassembly of actin fibers. This leads to a cytoskeletal collapse in the filopodia of tip cells, specialized endothelial cells which are directing the growth of new vessels and prevents vascular regeneration of ischemic areas in the retina. The inventors have shown that modulating the vasorepulsive action with a neutralizing Sema3A-antibody would increase the number of tip cells and redirect angiogenesis towards ischemic regions, such as the pathologically enlarged foveal avascular zone in humans with diabetic macular ischemia.

Therefore, in a fourth aspect, the invention relates to an anti-Sema3A antibody or an antigen-binding fragment thereof for use in the treatment or prevention a diseases selected from the group consisting of retinopathy, ischemic retinopathy, diabetic retinopathy including proliferative diabetic retinopathy and non-proliferative diabetic retinopathy, diabetic macular edema, diabetic macular ischemia, age-related macular degeneration, retinitis pigmentosa, inherited retinal dystrophy, myopic degeneration, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome and Stargardt disease.

The anti-Sema3A antibody of the invention is in particular useful for treating or preventing diabetic retinopathy including proliferative diabetic retinopathy and non-proliferative diabetic retinopathy, ischemic retinopathy, diabetic macular edema, diabetic macular ischemia, age-related macular edema, retinal neovascularization and choroidal neovascularization.

In a preferred embodiment, said disease is diabetic macular ischemia and the antibody of the invention promotes vascular regeneration within the ischemic retina (revascularization) and prevents pathological neovascularization of the vitreous region of the eye.

In another preferred embodiment, said disease is diabetic macular edema and the antibody of the invention reduces permeability of blood retinal barrier.

In another preferred embodiment, the present invention provides an anti-Sema3A antibody or an antigen-binding fragment thereof for inhibiting Sema3A-induced permeability of the blood retinal barrier and/or Sema3A-induced vasoregression from ischemic areas.

In a preferred aspect, the antibody of the invention is useful for the treatment of diabetic macular edema (DME) and/or diabetic macular ischemia (DMI). In a preferred embodiment, the antibody of the invention is useful for treating a patient suffering from DME and DMI. Preferably, the antibody of the invention is used for treating DMI as defined by over 15%, 20%, 25%, and more preferably 30% enlargement of foveal avascular zone (FAZ).

In a fifth aspect, the present invention provides a pharmaceutical composition comprising an anti-Sema3A antibody or an antigen-binding fragment thereof and a pharmaceutically acceptable carrier.

The anti-Sema3A antibody or an antigen-binding fragment thereof is administered by any suitable means, including intravitreal, oral, parenteral, subcutaneous, intraperitoneal, intrapulmonary, and intranasal. Parenteral infusions include intramuscular, intravenous, intraarterial, intraperitoneal, or subcutaneous administration. In addition, the anti-Sema3A antibody is suitably administered by pulse infusion, particularly with declining doses of the antibody. In one aspect, the dosing is given by injections, most preferably intravenous or subcutaneous injections, depending in part on whether the administration is brief or chronic. Preferably, the anti-Sema3A antibody is given through an intravitreal injection into the eye.

For the prevention or treatment of disease, the appropriate dosage of antibody will depend on a variety of factors such as the type of disease to be treated, as defined above, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments.

In a preferred embodiment, the dose range of the antibodies of the invention applicable per injection is usually from 1 mg/eye to 10 mg/eye, preferably between 1.5 mg/eye and 5 mg/eyes, more preferably between 2 mg/eye and 3 mg/eye and even more preferably about 2.5 mg/eye.

The term "suppression" is used herein in the same context as "amelioration" and "alleviation" to mean a lessening or diminishing of one or more characteristics of the disease.

The antibody composition will be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutically effective amount" of the antibody to be administered will be governed by such considerations, and is the minimum amount necessary to prevent, ameliorate, or treat the eye or retinal diseases addressed by the antibody of the invention.

The antibody need not be, but is optionally, formulated with one or more agents currently used to prevent or treat the disorder in question. The effective amount of such other agents depends on the amount of anti-Sema3A antibody present in the formulation, the type of disorder or treatment, and other factors discussed above. These are generally used in the same dosages and with administration routes as used hereinbefore or about from 1 to 99% of the heretofore employed dosages.

In another aspect, the invention also relates to an anti-Sema3A antibody or an antigen-binding fragment for use for the treatment or the prevention of non-ophthalmologic diseases, such as autoimmune arthritis, neuropathic pain, osteoporosis, and cancer.

Method of Treatment

In another aspect, the invention also encompasses any method for treating or preventing an eye or ocular diseases in a patient in need thereof, said method comprising the administration of an anti-Sema3A antibody of the invention.

Preferably, the invention relates to a method of using an antibody according to the invention for inhibiting the vasorepressive effect of SemaA3. More preferably, the invention relates to said method for improving revascularisation of the retina.

Preferably, the invention relates to a method for treating or preventing an eye or a retinal disease comprising administering to a patient in need thereof a pharmaceutically effective amount of the antibody according to the invention. Preferably, said disease is selected from the group consisting of retinopathy, ischemic retinopathy, diabetic retinopathy including proliferative diabetic retinopathy and non-proliferative diabetic retinopathy, diabetic macular edema, diabetic macular ischemia, age-related macular degeneration, retinitis pigmentosa, inherited retinal dystrophy, myopic degeneration, retinal artery occlusions, endophthalmitis, uveitis, cystoid macular edema, choroidal neovascular membrane secondary to any retinal diseases, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease. More preferably, said disease is selected from the group consisting of diabetic retinopathy including proliferative diabetic retinopathy and non-proliferative diabetic retinopathy, ischemic retinopathy, diabetic macular edema, diabetic macular ischemia, age-related macular edema, retinal neovascularization, glaucoma and choroidal neovascularization. In a yet preferably embodiment, said disease is diabetic macular edema and/or diabetic macular ischemia.

All the disclosed technical features described herein are applicable to said method of treatment.

Pharmaceutical Compositions and Administration Thereof

A composition comprising an anti-Sema3A antibody or an antigen-binding fragment thereof can be administered to a subject having or at risk of having an eye or retinal disease. The invention further provides for the use of an anti-Sema3A antibody or an antigen-binding fragment thereof in the manufacture of a medicament for prevention or treatment of a having an eye or retinal disease or Sema3A disease. All the disclosed technical features described herein are applicable to said use of an anti-Sema3A antibody or an antigen-binding fragment thereof in the manufacture of a medicament. The term "subject" as used herein means any mammalian patient to which an anti-Sema3A antibody or an antigen-binding fragment thereof can be administered, including, e.g., humans and non-human mammals, such as primates, rodents, and dogs. Subjects specifically intended for treatment using the methods described herein include humans. The anti-Sema3A antibody or an antigen-binding fragment thereof can be administered either alone or in combination with other compositions.

Various delivery systems are known and can be used to administer the anti-Sema3A antibody or an antigen-binding fragment thereof. Methods of introduction include but are not limited to intravitreal, eye drops, intradermal, intramuscular, intraperitoneal, intravenous, subcutaneous, intranasal, epidural, and oral routes. The anti-Sema3A antibody or an antigen-binding fragment thereof can be administered, for example by infusion, bolus or injection, and can be administered together with other biologically active agents. Administration can be systemic or local. In preferred embodiments, the administration is by intravitreal injection. Formulations for such injections may be prepared in, for example, prefilled syringes.

An anti-Sema3A antibody or an antigen-binding fragment thereof can be administered as pharmaceutical compositions comprising a therapeutically effective amount of the anti-Sema3A antibody or an antigen-binding fragment thereof and one or more pharmaceutically compatible ingredients.

In typical embodiments, the pharmaceutical composition is formulated in accordance with routine procedures as a pharmaceutical composition adapted for intravenous or subcutaneous administration to human beings. Typically, compositions for administration by injection are solutions in sterile isotonic aqueous buffer. Where necessary, the pharmaceutical can also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the pharmaceutical is to be administered by infusion, it can be dispensed with an infusion bottle containing sterile pharmaceutical grade water or saline. Where the pharmaceutical is administered by injection, an ampoule of sterile water for injection or saline can be provided so that the ingredients can be mixed prior to administration.

Further, the pharmaceutical composition can be provided as a pharmaceutical kit comprising (a) a container containing an anti-Sema3A antibody or an antigen-binding fragment thereof in lyophilized form and (b) a second container containing a pharmaceutically acceptable diluent (e.g., sterile water) for injection. The pharmaceutically acceptable diluent can be used for reconstitution or dilution of the lyophilized anti-Sema3A antibody or an antigen-binding fragment thereof. Optionally associated with such container(s) can be a notice in the form prescribed by a governmental agency regulating the manufacture, use or sale of pharmaceuticals or biological products, which notice reflects approval by the agency of manufacture, use or sale for human administration.

The amount of the anti-Sema3A antibody or an antigen-binding fragment thereof that is effective in the treatment or prevention of an eye or retinal disease can be determined by standard clinical techniques. In addition, in vitro assays may optionally be employed to help identify optimal dosage ranges. The precise dose to be employed in the formulation will also depend on the route of administration, and the stage of disorder, and should be decided according to the judgment of the practitioner and each patient's circumstances. Effective doses may be extrapolated from dose-response curves derived from in vitro or animal model test systems.

For example, toxicity and therapeutic efficacy of the anti-Sema3A antibody or an antigen-binding fragment thereof can be determined in cell cultures or experimental animals by standard pharmaceutical procedures for determining the $ED_{50}$ (the dose therapeutically effective in 50% of the population). An anti-Sema3A antibody or an antigen-binding fragment thereof that exhibits a large therapeutic index is preferred.

The data obtained from the cell culture assays and animal studies can be used in formulating a range of dosage for use in humans. The dosage of the anti-Sema3A antibody or an antigen-binding fragment thereof typically lies within a range of circulating concentrations that include the $ED_{50}$ with little or no toxicity. The dosage may vary within this range depending upon the dosage form employed and the route of administration utilized. For any anti-Sema3A antibody or an antigen-binding fragment thereof used in the method, the therapeutically effective dose can be estimated initially from cell culture assays. A dose can be formulated in animal models to achieve a circulating plasma concentration range that includes the $IC_{50}$ (i.e., the concentration of the test compound that achieves a half-maximal inhibition of symptoms) as determined in cell culture. Such information can be used to more accurately determine useful doses in humans. Levels in plasma can be measured, for example, by high performance liquid chromatography, ELISA and the like.

For intravitreal injection of the anti-Sema3A antibody, generally longer intervals between treatments are preferred. Due to its improved binding affinity and potency, the anti-Sema3A antibodies of the present invention can be administered in longer intervals.

In one embodiment the anti-Sema3A antibody is administered every 6 weeks, preferably every 7 weeks, preferably every 8 weeks, preferably every 9 weeks, preferably every 10 weeks, preferably every 11 weeks, and more preferably every 12 weeks. In a yet preferred embodiment, the anti-Sema3A antibody of the invention is administered once every 3 months.

Since the volume that can be administered to the eye is strictly limited, it is very important that an anti-Sema3A antibody can be formulated to high concentrations. Furthermore, potency of the anti-Sema3A antibody is of great importance as a potent antibody can exert its effect at even lower doses and thereby prolong activity and also intervals between treatments.

Antibodies of the present invention can be formulated to very high doses which include, but are not limited to 20 mg/ml, 30 mg/ml, 40 mg/ml, 50 mg/ml, 60 mg/ml, 70 mg/ml, 80 mg/ml, 90 mg/ml, or 100 mg/ml. Preferably, antibodies of the present invention can be formulated in a liquid formulation of about 50 mg/ml.

A typical dosage that can be administered to a patient is about 2.5 mg/eye. Typical buffer components that can be used for such a formulation comprise e.g. Sodium Acetate, PS20, and Trehalose Dihydrate.

In one embodiment, the anti-Sema3A antibody is formulated with 10 mM histidine buffer, 240 mM sucrose, 0.02 w/v % polysorbate 20 at pH 5.5 with a final protein concentration of 60 mg/mL.

In some embodiments, the pharmaceutical compositions comprising the anti-Sema3A antibody or an antigen-binding fragment thereof can further comprise a therapeutic agent, either conjugated or unconjugated to the binding agent.

With respect to therapeutic regimens for combinatorial administration, in a specific embodiment, an anti-Sema3A antibody or an antigen-binding fragment thereof is administered concurrently with a therapeutic agent. In another specific embodiment, the therapeutic agent is administered prior or subsequent to administration of the anti-Sema3A antibody or an antigen-binding fragment thereof, by at least an hour and up to several months, for example at least an hour, five hours, 12 hours, a day, a week, a month, or three months, prior or subsequent to administration of the anti-Sema3A antibody or an antigen-binding fragment thereof.

Polynucleotides, Vectors, Host Cells, and Recombinant Methods

In a sixth aspect, the present invention encompasses isolated polynucleotides that comprise a sequence encoding an anti-Sema3A antibody, vectors, and host cells comprising the polynucleotides, and recombinant techniques for production of the antibody. The isolated polynucleotides can encode any desired form of the anti-Sema3A antibody including, for example, full length monoclonal antibodies, Fab, Fab', F(ab')$_2$, and Fv fragments, diabodies, linear antibodies, single-chain antibody molecules, and multispecific antibodies formed from antibody fragments.

The polynucleotide(s) that comprise a sequence encoding an anti-Sema3A antibody or a fragment or chain thereof can be fused to one or more regulatory or control sequence, as known in the art, and can be contained in suitable expression vectors or host cell as known in the art. Each of the polynucleotide molecules encoding the heavy or light chain variable domains can be independently fused to a polynucleotide sequence encoding a constant domain, such as a human constant domain, enabling the production of intact antibodies. Alternatively, polynucleotides, or portions thereof, can be fused together, providing a template for production of a single chain antibody.

For recombinant production, a polynucleotide encoding the antibody is inserted into a replicable vector for cloning (amplification of the DNA) or for expression. Many suitable vectors for expressing the recombinant antibody are available. The vector components generally include, but are not limited to, one or more of the following: a signal sequence, an origin of replication, one or more marker genes, an enhancer element, a promoter, and a transcription termination sequence.

The anti-Sema3A antibodies can also be produced as fusion polypeptides, in which the antibody is fused with a heterologous polypeptide, such as a signal sequence or other polypeptide having a specific cleavage site at the amino terminus of the mature protein or polypeptide. The heterologous signal sequence selected is typically one that is recognized and processed (i.e., cleaved by a signal peptidase) by the host cell. For prokaryotic host cells that do not recognize and process the anti-Sema3A antibody signal sequence, the signal sequence can be substituted by a prokaryotic signal sequence. The signal sequence can be, for example, alkaline phosphatase, penicillinase, lipoprotein, heat-stable enterotoxin II leaders, and the like. For yeast secretion, the native signal sequence can be substituted, for example, with a leader sequence obtained from yeast invertase alpha-factor (including *Saccharomyces* and *Kluyveromyces* α-factor leaders), acid phosphatase, *C. albicans* glucoamylase, or the signal described in WO90/13646. In mammalian cells, mammalian signal sequences as well as viral secretory leaders, for example, the herpes simplex gD signal, can be used. The DNA for such precursor region is ligated in reading frame to DNA encoding the humanized anti-Sema3A antibody.

Expression and cloning vectors contain a nucleic acid sequence that enables the vector to replicate in one or more selected host cells. Generally, in cloning vectors this sequence is one that enables the vector to replicate independently of the host chromosomal DNA, and includes origins of replication or autonomously replicating sequences. Such sequences are well known for a variety of bacteria, yeast, and viruses. The origin of replication from the plasmid pBR322 is suitable for most Gram-negative bacteria, the 2-υ. plasmid origin is suitable for yeast, and various viral origins (SV40, polyoma, adenovirus, VSV, and BPV) are useful for cloning vectors in mammalian cells. Generally, the origin of replication component is not needed for mammalian expression vectors (the SV40 origin may typically be used only because it contains the early promoter).

Expression and cloning vectors may contain a gene that encodes a selectable marker to facilitate identification of expression. Typical selectable marker genes encode proteins that confer resistance to antibiotics or other toxins, e.g., ampicillin, neomycin, methotrexate, or tetracycline, or alternatively, are complement auxotrophic deficiencies, or in other alternatives supply specific nutrients that are not present in complex media, e.g., the gene encoding D-alanine racemase for Bacilli.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid, and hygromycin. Common selectable markers for mammalian cells are those that enable the identification of cells competent to take up a nucleic acid encoding a humanized anti-Sema3A antibody, such as DHFR (dihydrofolate reductase), thymidine kinase, metallothionein-I and -II (such as primate metallothionein genes), adenosine deaminase, ornithine decarboxylase, and the like. Cells transformed with the DHFR selection gene are first identified by culturing all of the transformants in a culture medium that contains methotrexate (Mtx), a competitive antagonist of DHFR. An appropriate host cell when wild-type DHFR is employed is the Chinese hamster ovary (CHO) cell line deficient in DHFR activity (e.g., DG44).

Alternatively, host cells (particularly wild-type hosts that contain endogenous DHFR) transformed or co-transformed with DNA sequences encoding anti-Sema3A antibody, wild-type DHFR protein, and another selectable marker such as aminoglycoside 3'-phosphotransferase (APH), can be selected by cell growth in medium containing a selection agent for the selectable marker such as an aminoglycosidic antibiotic, e.g., kanamycin, neomycin, or G418. See, e.g., U.S. Pat. No. 4,965,199.

Where the recombinant production is performed in a yeast cell as a host cell, the TRP1 gene present in the yeast plasmid YRp7 (Stinchcomb et al., 1979, Nature 282: 39) can be used as a selectable marker. The TRP1 gene provides a selection marker for a mutant strain of yeast lacking the ability to grow in tryptophan, for example, ATCC No. 44076 or PEP4-1 (Jones, 1977, Genetics 85:12). The presence of the trpl lesion in the yeast host cell genome then provides an effective environment for detecting transformation by growth in the absence of tryptophan. Similarly, Leu2p-deficient yeast strains such as ATCC 20,622 and 38,626 are complemented by known plasmids bearing the LEU2 gene.

In addition, vectors derived from the 1.6 μm circular plasmid pKD1 can be used for transformation of *Kluyveromyces* yeasts. Alternatively, an expression system for large-scale production of recombinant calf chymosin was reported for *K. lactis* (Van den Berg, 1990, Bio/Technology 8:135). Stable multi-copy expression vectors for secretion of mature recombinant human serum albumin by industrial strains of *Kluyveromyces* have also been disclosed (Fleer et al., 1991, Bio/Technology 9:968-975).

Expression and cloning vectors usually contain a promoter that is recognized by the host organism and is operably linked to the nucleic acid molecule encoding an anti-Sema3A antibody or polypeptide chain thereof. Promoters suitable for use with prokaryotic hosts include phoA promoter, β-lactamase and lactose promoter systems, alkaline phosphatase, tryptophan (trp) promoter system, and hybrid promoters such as the tac promoter. Other known bacterial promoters are also suitable. Promoters for use in bacterial systems also will contain a Shine-Dalgarno (S.D.) sequence operably linked to the DNA encoding the humanized anti-Sema3A antibody.

Many eukaryotic promoter sequences are known. Virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. All of these sequences are suitably inserted into eukaryotic expression vectors.

Examples of suitable promoting sequences for use with yeast hosts include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase.

Inducible promoters have the additional advantage of transcription controlled by growth conditions. These include yeast promoter regions for alcohol dehydrogenase 2, isocytochrome C, acid phosphatase, derivative enzymes associated with nitrogen metabolism, metallothionein, glyceraldehyde-3-phosphate dehydrogenase, and enzymes responsible for maltose and galactose utilization. Suitable vectors and promoters for use in yeast expression are further described in EP 73,657. Yeast enhancers also are advantageously used with yeast promoters.

Anti-Sema3A antibody transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, or from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., 1982, Nature 297:598-601, disclosing expression of human p-interferon cDNA in mouse cells under the control of a thymidine kinase promoter from herpes simplex virus. Alternatively, the rous sarcoma virus long terminal repeat can be used as the promoter.

Another useful element that can be used in a recombinant expression vector is an enhancer sequence, which is used to increase the transcription of a DNA encoding an anti-Sema3A antibody by higher eukaryotes. Many enhancer sequences are now known from mammalian genes (e.g., globin, elastase, albumin, α-fetoprotein, and insulin). Typically, however, an enhancer from a eukaryotic cell virus is used. Examples include the SV40 enhancer on the late side of the replication origin (bp 100-270), the cytomegalovirus early promoter enhancer, the polyoma enhancer on the late side of the replication origin, and adenovirus enhancers. See also Yaniv, 1982, Nature 297:17-18 for a description of enhancing elements for activation of eukaryotic promoters. The enhancer may be spliced into the vector at a position 5' or 3' to the anti-Sema3A antibody-encoding sequence, but is preferably located at a site 5' from the promoter.

Expression vectors used in eukaryotic host cells (yeast, fungi, insect, plant, animal, human, or nucleated cells from other multicellular organisms) can also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding anti-Sema3A antibody. One useful transcription termination component is the bovine growth hormone polyadenylation region. See WO94/11026 and the expression vector disclosed therein. In some embodiments, anti-Sema3A antibodies can be expressed using the CHEF system. (See, e.g., U.S. Pat. No. 5,888,809; the disclosure of which is incorporated by reference herein.)

Suitable host cells for cloning or expressing the DNA in the vectors herein are the prokaryote, yeast, or higher eukaryote cells described above. Suitable prokaryotes for this purpose include eubacteria, such as Gram-negative or Gram-positive organisms, for example, Enterobacteriaceae such as *Escherichia*, e.g., *E. coli, Enterobacter, Erwinia, Klebsiella, Proteus, Salmonella*, e.g., *Salmonella typhimurium, Serratia*, e.g., *Serratia marcescans*, and *Shigella*, as well as Bacilli such as *B. subtilis* and *B. licheniformis* (e.g., *B. licheniformis* 41 P disclosed in DD 266,710 published Apr. 12, 1989), *Pseudomonas* such as *P. aeruginosa*, and *Streptomyces*. One preferred *E. coli* cloning host is *E. coli* 294 (ATCC 31,446), although other strains such as *E. coli* B, *E. coli* X1776 (ATCC 31,537), and *E. coli* W3110 (ATCC 27,325) are suitable. These examples are illustrative rather than limiting.

In addition to prokaryotes, eukaryotic microbes such as filamentous fungi or yeast are suitable cloning or expression hosts for anti-Sema3A antibody-encoding vectors. *Saccharomyces cerevisiae*, or common baker's yeast, is the most commonly used among lower eukaryotic host microorganisms. However, a number of other genera, species, and strains are commonly available and useful herein, such as *Schizosaccharomyces pombe; Kluyveromyces* hosts such as, e.g., *K. lactis, K. fragilis* (ATCC 12,424), *K. bulgaricus* (ATCC 16,045), *K. wickeramii* (ATCC 24,178), *K. waltii* (ATCC 56,500), *K. drosophilarum* (ATCC 36,906), *K. thermotolerans*, and *K. marxianus; yarrowia* (EP 402,226); *Pichia pastors* (EP 183,070); *Candida; Trichoderma reesia* (EP 244,234); *Neurospora crassa; Schwanniomyces* such as *Schwanniomyces occidentalis*; and filamentous fungi such as, e.g., *Neurospora, Penicillium, Tolypocladium,* and *Aspergillus* hosts such as *A. nidulans* and *A. niger*.

Suitable host cells for the expression of glycosylated anti-Sema3A antibody are derived from multicellular organisms. Examples of invertebrate cells include plant and insect cells, including, e.g., numerous baculoviral strains and variants and corresponding permissive insect host cells from hosts such as *Spodoptera frugiperda* (caterpillar), *Aedes aegypti* (mosquito), *Aedes albopictus* (mosquito), *Drosophila melanogaster* (fruitfly), and *Bombyx mori* (silk worm). A variety of viral strains for transfection are publicly available, e.g., the L-1 variant of *Autographa californica* NPV and the Bm-5 strain of *Bombyx mori* NPV, and such viruses may be used, particularly for transfection of *Spodoptera frugiperda* cells.

Plant cell cultures of cotton, corn, potato, soybean, petunia, tomato, and tobacco can also be utilized as hosts.

The anti-Sema3A antibody of the invention can also be incorporated in viral vectors, i.e. the polynucleotide encoding for the anti-Sema3A antibody or an antigen-binding fragment thereof is introduced into the viral vector and then expressed in the body of the patient after infection with the virus.

In another aspect, expression of anti-Sema3A antibody is carried out in vertebrate cells. The propagation of vertebrate cells in culture (tissue culture) has become routine procedure and techniques are widely available. Examples of useful mammalian host cell lines are monkey kidney CV1 line transformed by SV40 (COS-7, ATCC CRL 1651), human embryonic kidney line (293 or 293 cells subcloned for growth in suspension culture, (Graham et al., 1977, J. Gen Virol. 36: 59), baby hamster kidney cells (BHK, ATCC CCL 10), Chinese hamster ovary cells/-DHFR1 (CHO, Urlaub et al., 1980, Proc. Natl. Acad. Sci. USA 77: 4216; e.g., DG44), mouse sertoli cells (TM4, Mather, 1980, Biol. Reprod. 23:243-251), monkey kidney cells (CV1 ATCC CCL 70), African green monkey kidney cells (VERO-76, ATCC CRL-1587), human cervical carcinoma cells (HELA, ATCC CCL 2), canine kidney cells (MDCK, ATCC CCL 34), buffalo rat liver cells (BRL 3A, ATCC CRL 1442), human lung cells (W138, ATCC CCL 75), human liver cells (Hep G2, HB 8065), mouse mammary tumor (MMT 060562, ATCC CCL51), TR1 cells (Mather et al., 1982, Annals N.Y. Acad. Sci. 383: 44-68), MRC 5 cells, FS4 cells, and human hepatoma line (Hep G2).

Host cells are transformed with the above-described expression or cloning vectors for anti-Sema3A antibody production and cultured in conventional nutrient media modified as appropriate for inducing promoters, selecting transformants, or amplifying the genes encoding the desired sequences.

The host cells used to produce anti-Sema3A antibody described herein may be cultured in a variety of media. Commercially available media such as Ham's F10 (Sigma-Aldrich Co., St. Louis, Mo.), Minimal Essential Medium ((MEM), (Sigma-Aldrich Co.), RPMI-1640 (Sigma-Aldrich Co.), and Dulbecco's Modified Eagle's Medium ((DMEM), Sigma-Aldrich Co.) are suitable for culturing the host cells. In addition, any of the media described in one or more of Ham et al., 1979, Meth. Enz. 58: 44, Barnes et al., 1980, Anal. Biochem. 102: 255, U.S. Pat. Nos. 4,767,704, 4,657, 866, 4,927,762, 4,560,655, 5,122,469, WO 90/103430, and WO 87/00195 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as gentamicin), trace elements (defined as inorganic compounds usually present at final concentrations in the micromolar range), and glucose or an equivalent energy source. Other supplements may also be included at appropriate concentrations that would be known to those skilled in the art. The culture conditions, such as temperature, pH, and the like, are those previously used with the host cell selected for expression, and will be apparent to the ordinarily skilled artisan.

When using recombinant techniques, the antibody can be produced intracellularly, in the periplasmic space, or directly secreted into the medium. If the antibody is produced intracellularly, the cells may be disrupted to release protein as a first step. Particulate debris, either host cells or lysed fragments, can be removed, for example, by centrifugation or ultrafiltration. Carter et al., 1992, Bio/Technology 10:163-167 describes a procedure for isolating antibodies that are secreted to the periplasmic space of *E. coli*. Briefly, cell paste is thawed in the presence of sodium acetate (pH 3.5), EDTA, and phenylmethylsulfonylfluoride (PMSF) over about 30 minutes. Cell debris can be removed by centrifugation. Where the antibody is secreted into the medium, supernatants from such expression systems are generally first concentrated using a commercially available protein concentration filter, for example, an Amicon or Millipore Pellicon ultrafiltration unit. A protease inhibitor such as PMSF may be included in any of the foregoing steps to inhibit proteolysis and antibiotics may be included to prevent the growth of adventitious contaminants. A variety of methods can be used to isolate the antibody from the host cell.

The antibody composition prepared from the cells can be purified using, for example, hydroxylapatite chromatography, gel electrophoresis, dialysis, and affinity chromatography, with affinity chromatography being a typical purification technique. The suitability of protein A as an affinity ligand depends on the species and isotype of any immunoglobulin Fc domain that is present in the antibody. Protein A can be used to purify antibodies that are based on human gamma1, gamma2, or gamma4 heavy chains (see, e.g., Lindmark et al., 1983 J. Immunol. Meth. 62:1-13). Protein G is recommended for all mouse isotypes and for human gamma3 (see, e.g., Guss et al., 1986 EMBO J. 5:1567-1575). A matrix to which an affinity ligand is attached is most often agarose, but other matrices are available. Mechanically stable matrices such as controlled pore glass or poly(styrenedivinyl)benzene allow for faster flow rates and shorter processing times than can be achieved with agarose. Where the antibody comprises a $C_{H3}$ domain, the Bakerbond ABX™ resin (J. T. Baker, Phillipsburg, N.J.) is useful for purification. Other techniques for protein purification such as fractionation on an ion-exchange column, ethanol precipitation, reverse phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to low pH hydrophobic interaction chromatography using an elution buffer at a pH between about 2.5-4.5, typically performed at low salt concentrations (e.g., from about 0-0.25M salt).

Also included are nucleic acids that hybridize under low, moderate, and high stringency conditions, as defined herein, to all or a portion (e.g., the portion encoding the variable region) of the nucleotide sequence represented by isolated polynucleotide sequence(s) that encode an Sema3A-antibody or antibody fragment. The hybridizing portion of the hybridizing nucleic acid is typically at least 15 (e.g., 20, 25, 30 or 50) nucleotides in length. The hybridizing portion of the hybridizing nucleic acid is at least 80%, e.g., at least 90%, at least 95%, or at least 98%, identical to the sequence of a portion or all of a nucleic acid encoding an anti-Sema3A polypeptide (e.g., a heavy chain or light chain variable region), or its complement. Hybridizing nucleic acids of the type described herein can be used, for example, as a cloning probe, a primer, e.g., a PCR primer, or a diagnostic probe.

In one embodiment, the present invention relates to an isolated polynucleotide or polynucleotides comprising a sequence encoding a heavy chain as shown in SEQ ID NO: 14, SEQ ID NO: 16, SEQ ID NO: 17, or SEQ ID NO: 19 or a heavy chain variable region as shown in SEQ ID NO: 7, SEQ ID NO: 8, SEQ ID NO: 9 or SEQ ID NO: 10; and a sequence encoding a light chain as shown in SEQ ID NO: 15, SEQ ID NO: 18 or SEQ ID NO: 20 or a light chain variable region as shown in SEQ ID NO: 11, SEQ ID NO: 12 or SEQ ID NO: 13.

It is to be understood that in said anti-Sema3A antibodies and antibody fragments the nucleic acid sequence coding for the CDRs remain unchanged (unchanged with respect to the amino acid they encode, equivalents of the DNA sequence due to the degeneracy of codons are possible) but the surrounding regions e.g. FR regions can be engineered.

Articles of Manufacture

In another aspect, an article of manufacture containing materials useful for the treatment of the disorders described above is included. The article of manufacture comprises a container and a label. Suitable containers include, for example, bottles, vials, syringes, and test tubes. The containers may be formed from a variety of materials such as glass or plastic. The container holds a composition that is effective for treating the condition and may have a sterile access port. For example, the container may be an intravenous solution bag or a vial having a stopper pierceable by a hypodermic injection needle. The active agent in the composition is the anti-Sema3A antibody or the antigen-binding fragment thereof. The label on or associated with the container indicates that the composition is used for treating the condition of choice. The article of manufacture may further comprise a second container comprising a pharmaceutically-acceptable buffer, such as phosphate-buffered saline, Ringer's solution, and dextrose solution. It may further include other materials desirable from a commercial and user standpoint, including other buffers, diluents, filters, needles, syringes, and package inserts with instructions for use.

The invention is further described in the following examples, which are not intended to limit the scope of the invention.

EXAMPLES

Example 1: Upregulation of Sema3A in the Vitreous of DME and PDR Patients

The expression of Sema3A in the retina of samples from human donors with a history of Diabetic Retinopathy was investigated by immunohistochemistry. The immunostaining protocol was as follows:
1. Thaw slides and let samples air dry for 30 min at room temperature (RT);
2. Draw pap pen box and let dry;
3. Antigen retrieval in 1% SDS for 5 min at RT;
4. Wash slides 3 times in PBS for 5 min;
5. Block sections in 1% BSA/0.3% Triton X100/PBS solution (blocking solution) for 30 min at RT;
6. Dilute rabbit-anti Sema3a (abcam, ab23393) 1st antibody 1:200 in blocking solution. Incubate sections on slide at RT overnight;
7. Rinse slides 3 times in PBS for 5 min;
8. 2nd antibody incubation with donkey anti-rabbit Alexa fluor546 (invitrogen, A10040) at 1:400 dilution in DAPI/0.3% Triton X100/PBS solution. Incubate sections on slide for 3 hours at RT;
9. Rinse slides 3-5 times in PBS for 5 min;
10. Coverslip sections with Aquamount and let air dry;
11. Image sections and grade intensity at 40× magnification.

Figure 1A:
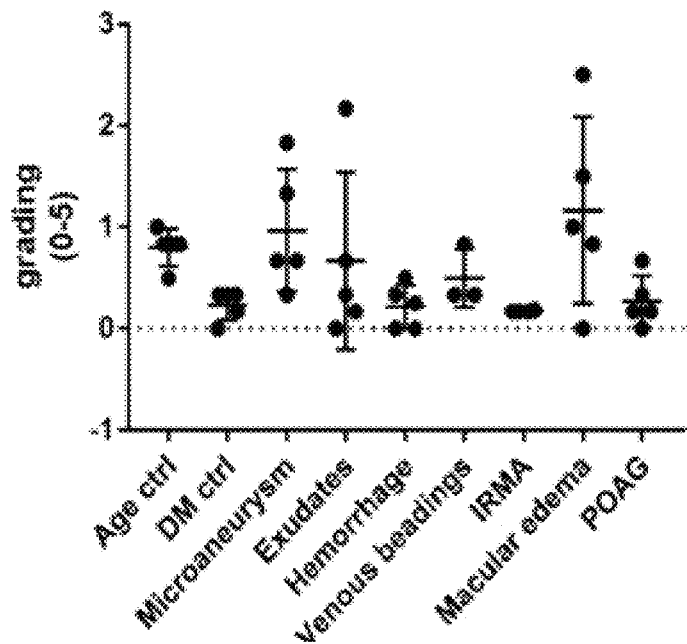
FIGS. 1A and 1B show the localization of Sema3A in human eyes.
Figure 1B:
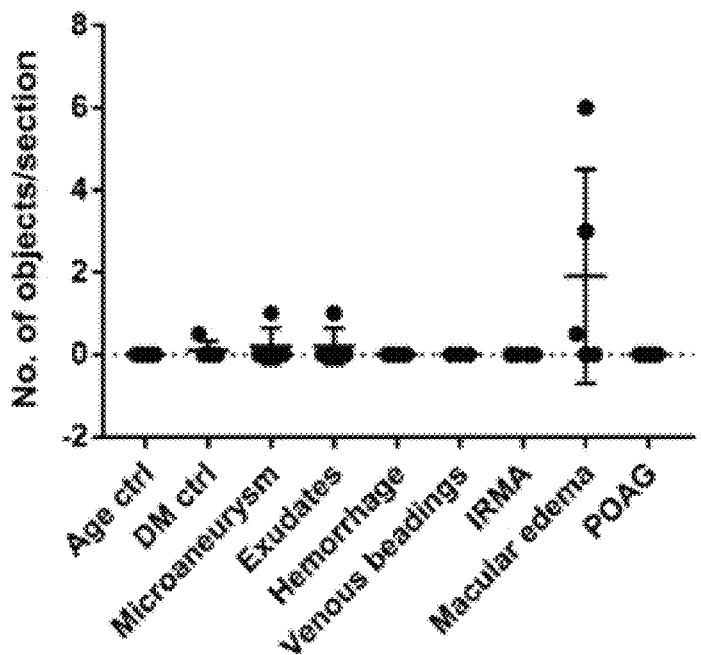

Sets of three sections per each human donor were immunostained for Sema3A. The Sema3A labelling was independently evaluated in each of these regions by observers previously trained for this specific task using a 5-point grading scheme (0=no detection, 1=low intensity, few spots, 2=moderate intensity, several spots, 3=bright intensity, widespread staining and 4=very bright intensity, abundant detection). The observers were unaware of the health status of the eye donors. Within the retina, Sema3A was associated with the vasculature wall of retinal blood vessels. The expression of Sema3A in retinal vasculature and retinal parenchyma was increased in patients with diabetic macular edema compared to diabetics without ocular pathology (FIG. 1).

Example 2: Efficacy in Cellular Permeability Assay

Transcellular permeability was measured by the penetration of FITC-dextran in monolayers of human retinal microvascular endothelial cells (HRMEC).

Briefly, in vitro endothelial permeability was measured using a Millipore kit ('In Vitro Vascular Permeability Assay' Catalog No. ECM642) and human retinal microvascular endothelial cells (HRMEC). The Assay kit provides a 96-well receiver plate with cell culture inserts. The inserts contain 1 µm pores and are coated with type I rat-tail collagen. HRMEC were seeded at a density of 25000 cells/well onto the inserts and cells were allowed to grow into a monolayer for 3 days. Cells were treated with recombinant VEGF-A, Sema3A as well as an antibody according to the invention over night. A high molecular weight FITC-Dextran solution provided within the kit was added to the insert, allowing the fluorescent molecules to pass through the endothelial cell monolayer. In vitro permeability was determined by measuring the fluorescence of the receiver plate well solution at 485 nm/535 nM (excitation and absorption).

The inventors tested an exemplary antibody according to the invention: clone I. Said antibody comprises a heavy chain comprising the amino acid sequence of SEQ ID NO: 14 and a light chain comprising the amino acid sequence of SEQ ID NO: 15.

Figure 2:
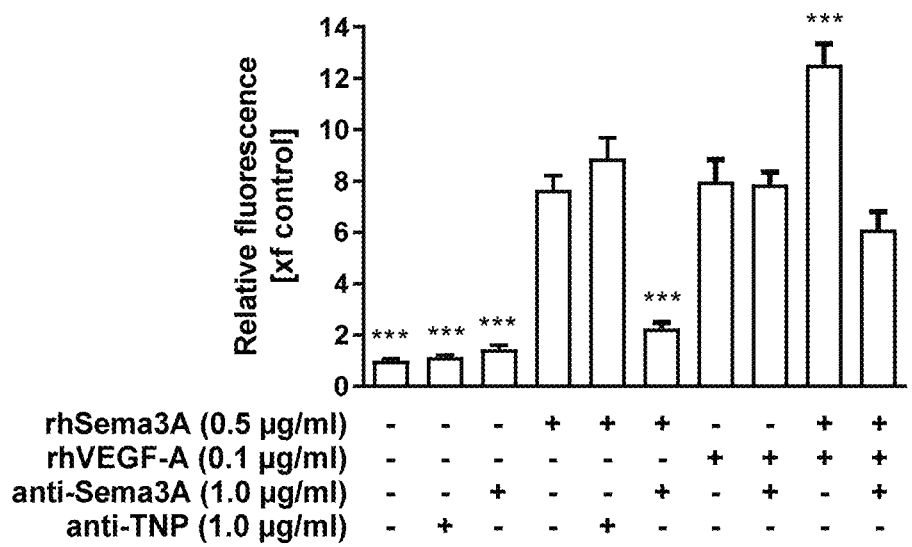
FIG. 2 shows the efficacy of an anti-Sema3A antibody according to the invention in cellular permeability assay. Transcellular permeability was measured by the penetration of FITC-dextran in monolayers of human retinal microvascular endothelial cells (HRMEC). Cells were treated with an agent: recombinant VEGF-A ("rhVEGF-A"), recombinant Sema3A ("rhSema3A"), antibody according to the invention or an antibody directed against TNP used a control (anti-Sema3A). In the figure a sign (+) signifies that cells were treated with the corresponding agent. A sign (−) indicates that the cells were not treated with the corresponding agent. In vitro permeability was determined by measuring the fluorescence. The anti-Sema3A antibody according to the invention completely inhibited the permeability induced by Sema3A, but not the permeability induced by VEGF-A. Importantly, the permeability effect of Sema3A is independent from VEGF-A. The use of a control antibody directed against TNP confirms that the effect is due to the specific target of Sema3A by the antibody of the invention. Permeation of FITC-dextran in human retinal microvascular endothelial cells is measured in a transwell assay. Anti-TNP is a control antibody against trinitrophenol. Anti-Sema3A is an antibody according to the invention (clone I). Significance is shown vs. recombinant human Sema3A.

The anti-Sema3A antibody according to the invention completely inhibited the permeability induced by Sema3A, but not the permeability induced by VEGF-A (FIG. 2). Importantly, the permeability effect of Sema3A is independent from VEGF-A. The use of a control antibody directed against TNP confirms that the effect is due to the specific target of Sema3A by the antibody of the invention.

Example 3: Measurement of Cytoskeletal Collapse in Cellular Assay

The cellular activity of an exemplary antibody according to the invention (clone I) was assessed by a measure of cytoskeletal collapse in human retinal microvascular endothelial cells (HRMEC) using the XCELLigence system (Real Time Cell Analysis Instruments. as commercialized by ACEA Biosciences). The system measures cell attachment and confluence via cellular impedance. HRMEC endogenously express Neuropilin-1 (Nrp1) and plexins, which are components of the class-3 Semaphorin holoreceptor. By binding to this receptor complex, semaphorins induce a collapse of F-actin fibers in the endothelium. In this functional assay, addition of recombinant Sema3A protein to a confluent layer of human retinal microvascular endothelial cells lowers cellular impedance due to the cytoskeletal collapse and subsequent shrinkage of the cells, measured as a reduction in cellular impedance.

Briefly, E-Plates View were coated with Attachment Factor. Cells were seeded with a density of 20000 cells/well and were then allowed to grow into a monolayer under their normal growth conditions inside the XCELLigence device overnight.

Sema3 (or other class-3 semaphorins) with and without the anti-Sema3A antibody according to the invention combinations were added in the presence of 3 mM CaCl2). The cell index was normalized to the time point before addition of substances. Calculations were done 5h after stimulation.

Figure 3:
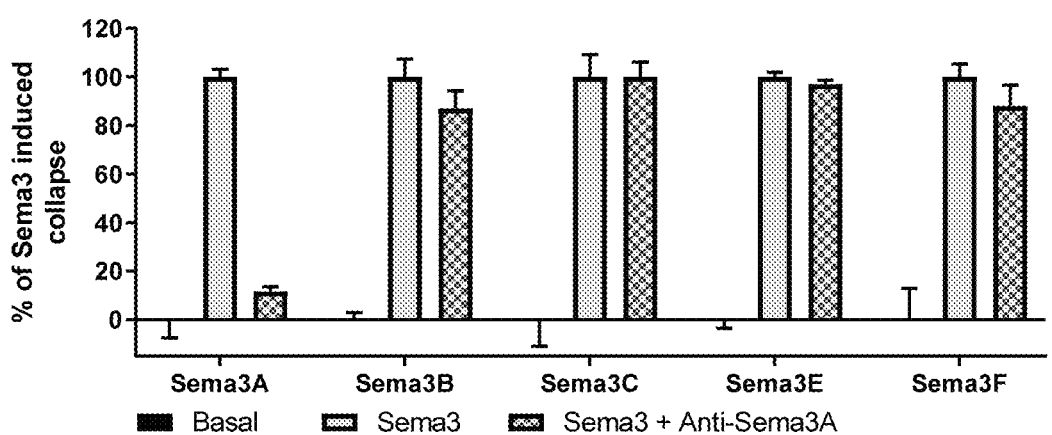
FIG. 3 shows cytoskeletal collapse in HRMEC (Xcelligence). Sema3A-F all induce a cytoskeletal collapse in human retinal endothelial cells. The antibody of the invention (clone I) is specific for Sema3A and prevents only the Sema3A-induced collapse.

The cytoskeletal collapse induced by Sema3A can be completely prevented by the anti-Sema3A antibody according to the invention. A cytoskeletal collapse induced by the other tested semaphorins (B, C, E and F) could not be prevented by the anti-Sema3A antibody according to the invention, confirming its specificity of the antibody of the invention to Sema3A (FIG. 3).

Example 4: Affinity and Cellular Potency

A) Affinity

The running buffer for this experiment and all dilutions (except where stated) were done in PBS-T-EDTA with 0.01% Tween20 [100 µl of 100% Tween20 was added to 2 L of PBS-T-EDTA to make final Tween 20 concentration of 0.01%]. The GLM sensorchip was normalized and pre-conditioned as per the manufacturer's recommendations. The sensorchip was activated with equal mixture of EDC/s-NHS in the horizontal direction for 300 sec at a flow rate of 30 µl/min and immobilized with Human Fab Binder (10 µg/ml in 10 mM acetate pH 5.0) in the horizontal direction for 300 sec at a flowrate of 30 µl/min resulting in ~6739-7414 RU of Human Fab Binder on the surface. The sensorchip was deactivated with 1M ethanolamine HCl in the horizontal direction for 300 sec at a flowrate of 30 µl/min. The sensorchip was stabilized with 18 sec of 10 mM glycine, pH 2.1 at a flowrate of 100 µl/min 1 time horizontally and 1 time vertically.

The inventors tested an exemplary antibody according to the invention (clone I). Said antibody (0.5 µg/ml) was captured on the Human Fab Binder surface vertically for 300 sec at a flowrate of 25 µl/min resulting ~180 RU capture level. The baseline was stabilized by injecting PBS-T-EDTA for 60 sec at a flowrate of 40 µl/min horizontally. The analyte was injected horizontally over the captured antibody for 600 sec at a flowrate of 40 µl/min and a dissociation for 7200 sec. The concentrations of the analytes were 0 nM, 0.625 nM, 1.25 nM, 2.5 nM, 5 nM, and 10 nM. The surface was regenerated by injecting 10 mM glycine, pH 2.1 for 18 sec at a flowrate of 100 µl/min one time horizontally and one time vertically. PBS-T-EDTA was injected for 60 sec at a flowrate of 25 µl/min one time vertically.

The interspot (interactions with sensor surface) and blank (PBS-T-EDTA with 0.01% Tween20 or 0 nM analyte) were subtracted from the raw data. Sensorgrams were then fit globally to 1:1 Langmuir binding to provide on-rate (ka), off-rate (kd), and affinity ($K_D$) values.

B) Cellular Potency

For determination of a functional potency in the cytoskeletal collapse assay, Sema3A concentration response curves were combined with increasing concentrations of antibody as IC50 shift experiments. A Gaddum Schild plot was performed to calculate the pA2 value (the negative logarithm of the concentration of antibody needed to shift the Sema3A concentration response curve by factor 2). The potency in pM was calculated from the pA2 value as =POTENCY (10;-X).

The results are summarised in the table 6 below.

TABLE 6

| Molecule | Affinity ($K_d$) [pM] | | | | | Functional antagonism in cytoskeletal collapse assay ($A_2$) [pM] |
| | Human | Cyno | Mouse | Rat | Rabbit | Human |
|---|---|---|---|---|---|---|
| Antibody of the invention (clone I) | 29 | 28 | 27 | 27 | 42 | 69 |

Example 5: Assessment of the Immunogenicity of the Antibody of the Invention

The inventors have assessed the predicted immunogenicity of an exemplary antibody according to the invention, clone I. Said antibody comprises a heavy chain and a light chain comprising the amino acid sequences of SEQ ID NO: 14 and SEQ ID NO: 15 respectively.

For this purpose, they have used an in silico tool for predicting T cell epitopes (EpiMatrix developed by EpiVax).

By screening the sequences of many human antibody isolates, EpiVax has identified several highly conserved HLA ligands which are believed to have a regulatory potential. Experimental evidence suggests many of these peptides are, in fact, actively tolerogenic in most subjects. These highly conserved, regulatory, and promiscuous T cell epitopes are now known as Tregitopes (De Groot et al. Blood. 2008 Oct. 15; 112(8):3303-11). The immunogenic potential of neo-epitopes contained in humanized antibodies can be effectively controlled in the presence of significant numbers of Tregitopes.

For the purposes of antibody immunogenicity analysis, EpiVax has developed a Tregitope-adjusted EpiMatrix Score and corresponding prediction of anti-therapeutic antibody response. To calculate the Tregitope-adjusted EpiMatrix Score, the scores of the Tregitopes are deducted from the EpiMatrix Protein Score. The Tregitope-adjusted scores have been shown to be well correlated with observed clinical immune response for a set of 23 commercial antibodies (De Groot et al. Clin Immunol. 2009 May; 131(2):189-201).

The results on the EpiMatrix scale are summarised in the table 7 below.

TABLE 7

| Molecule | Heavy Chain (% human) | | Epivax | Epivax | Light chain (% human) | |
|---|---|---|---|---|---|---|
| | FR | V-gene | (VH) | (Vκ) | FR | V-gene |
| Antibody of the invention (clone I) | 97 | 91 | −27.27 | −21.79 | 98 | 88 |

Sequences of the antibody of the invention score on the low end of EpiMatrix scale, indicating that the antibody of the invention has a strongly limited potential for immunogenicity. Said EpiMatrix scale is well known by the person skilled in the art and can be found inter alia in FIG. 2 of the publication Mufarrege et al. Clin Immunol. 2017 March; 176:31-41.

Example 6: Efficacy on Tip Cell Density and Avascular Area In Vivo (Oxygen Induced Retinopathy OIR Model)

The effect of an exemplary antibody according to the invention (clone I) on revascularization of ischemic avascular area was investigated in a mouse model of oxygen-induced retinopathy (OIR). Litters of C57Bl/6J mice were exposed to an atmosphere of 75% oxygen from postnatal day 7 to postnatal day 12. This leads to a regression of blood vessels in the central retina and the formation of an avascular area. After returning to normoxic conditions, this area becomes ischemic. The pups receive a single intravitreal injection of 10 μg antibody in 0.5 μl solution in each eye under anaesthesia with isoflurane on postnatal day 12. On postnatal day 17, the animals are sacrificed and the eyes enucleated. Eyes are fixed in formalin and a retinal flatmount is prepared in which retinal blood vessels are stained with isolectin B4. The number of tip cells (specialized endothelial cells initiating the formation of new vessels) are counted at the avascular front along the whole retina (the boundary between vascularized peripheral area and avascular central area of the retina).

The tip cells were identified by their special morphology showing filopodia extensions. For analysis, the number of tip cells is normalized to the length of the avascular front. The size of the avascular area is determined using a confocal microscope and image analysis software.

The anti-Sema3A antibody of the invention increases the tip cell density in the mouse OIR model (FIG. 4). Furthermore, it shows a reduction of the avascular area. There is a negative correlation between the tip cell density and the size of the avascular area, indicating a mechanistic dependence of the two parameters. The use of a control antibody directed against TNP confirms that the effect is due to the specific target of Sema3A by the antibody of the invention.

Overall, the anti-Sema3A antibody reduces ischemic avascular area size in an animal model of oxygen induced retinopathy, indicating a beneficial effect Diabetic Macular Ischemia.

Example 7: Comparison of Anti-Sema3A and Avastin $t_{1/2}$ in Rabbit Eye

The results are summarised in the table 8 below.

TABLE 8

| | Calculated t½ (day) | | |
|---|---|---|---|
| | Antibody of the invention (clone I) | | |
| | 0-14 day | all | Avastin |
| Vitreous | 5.1 | 3.9 | 4.4 |
| Retina | 6.1 | 4.1 | 4.8 |
| Aqueous | 4.7 | 3.3 | 4.5 |

The calculated half-lives were 3.9, 4.1 and 3.3 days in vitreous, retina, and aqueous humor respectively. These half-lives are similar to those reported in the literature for the clinically used recombinant humanized monoclonal IgG1 antibody Avastin (anti-VEGF, bevacizumab, Bakri et al., Opthalmology, 2007), which were also confirmed experimentally in-house. These results were as expected, since the intravitreal clearance of full length IgGs depends mainly on their molecular size, which is similar for the antibody of the invention and Avastin. Therefore, the human PK, including the ocular half-life of the antibody of the invention and Avastin is expected to be similar. The reported human ocular half-life of Avastin is 9.73±1.48 days (Hutton-Smith, 2016).

Example 8: Comparison of Binding Affinity Between the Antibody of the Invention and Chiome Antibody For comparison purposes, the inventors have developed the humanized antibody directed against Sema3A disclosed in WO2014123186 (Chiome Bioscience) with the following features:
- the heavy chain is as shown in SEQ ID NO: 11 in WO2014123186, and
- the light chain is as shown in SEQ ID NO: 12 in WO2014123186.

The inventors have developed 2 forms of this antibody:
- one formatted on IgG1 KO Fc, referred to in the followings as "Chiome antibody A" and
- one formatted on IgG1 KO-FcRn null referred to in the followings as "Chiome antibody B".

A high surface density of anti-human Fab antibody (GE Healthcare) was immobilized over a GLM chip (BioRad) via direct amine coupling over 6 horizontal channels according to the BioRad manufacturer's manual.

The antibody of the invention (clone I) and Chiome antibodies were captured over the anti-human Fab antibody surface over 5 of 6 vertical channels with a minimum surface density for the kinetic binding assay. Human Sema3A was prepared in PBS-T-EDTA buffer (BioRad) at concentrations of 100, 50, 25, 12.5, 10, 6.25, 5, 2.5, 1.25, 0.625 and 0 nM. A PBS-T-EDTA buffer injection was used as a double reference for the kinetic data analysis. Each of the human Sema3A solutions and PBS-T-EDTA buffer were injected simultaneously over the 6 horizontal channels for 10 min at a flow rate of 40 µL/min followed by 2 hr dissociation phase. The surfaces were regenerated by an 18 sec injection of 10 mM pH 2.1 glycine HCl (GE Healthcare) at a flow rate of 100 µL/min followed by an injection of 60 sec PBS-T-EDTA at a flow rate of 25 L/min. The binding sensorgrams were fit to 1:1 langmuir model to calculate on-rate, off-rate, and affinity.

The Kinetic and affinity data of the antibody of the invention and the Chiome antibody binding to human Sema3A are listed in table 9 below.

TABLE 9

| Sample Name | KD to HuSema3A |
| --- | --- |
| Chiome Antibody A | 56.4 nM |
| Chiome Antibody B | 55.9 nM |
| Antibody of the invention (clone I) | 32.0 pM |

Conclusion

The results shows that the antibody of the invention proved to have superior binding affinity to human Sema3A than the prior art antibody disclosed by Chiome Bioscience.

Example 9: Comparison of Binding Affinity Between the Antibody of the Invention and Samsung scFv scFv fragments as disclosed in WO2017074013 (Samsung) have been compared.

For comparison purposes, the inventors have developed 3 disclosed fragments with the features disclosed in the table 10 below.

TABLE 10

| Name of the antibody | Sequences | SEQ ID NO as set forth in WO2017074013 |
| --- | --- | --- |
| Samsung scFv 1 | Heavy chain | 19 |
|  | Light chain | 20 |
| Samsung scFv 2 | Heavy chain | 21 |
|  | Light chain | 22 |
| Samsung scFv 3 | Heavy chain | 23 |
|  | Light chain | 24 |

A high surface density of anti-His antibody (GE Healthcare) was immobilized over a GLM chip (BioRad) via direct amine coupling over 6 horizontal channels according to the BioRad manufacturer's manual. The Samsung ScFv antibodies were captured over the anti-His antibody surface over 5 of 6 vertical channels with a minimum surface density for the kinetic binding assay. Human Sema3A was prepared in PBS-T-EDTA buffer (BioRad) at concentrations of 100, 50, 25, 12.5, 10, 6.25, 5, 2.5, 1.25, 0.625 and 0 nM. A PBS-T-EDTA buffer injection was used as a double reference for the kinetic data analysis. Each of the human Sema3A solutions and PBS-T-EDTA buffer were injected simultaneously over the 6 horizontal channels for 10 min at a flow rate of 40 µL/min followed by 1 hr dissociation phase. The surfaces were regenerated by an 18 sec injection of 10 mM pH 2.1 glycine HCl (GE Healthcare) at a flow rate of 100 µL/min followed by an injection of 60 sec PBS-T-EDTA at a flow rate of 25 µL/min. The binding sensorgrams were fit to 1:1 langmuir model to calculate on-rate, off-rate, and affinity.

The binding for the antibody of the invention to human Sema3A (clone I) was done using similar method but goat anti-human IgG (Invitrogen) was used to capture the antibody of the invention. Binding of the antibody of the invention and Samsung ScFv to Cynomology, mouse, rat, or rabbit Sema3A was also done using the same methods.

The Kinetic and affinity data of the antibody of the invention and the Samsung scFv are listed in the table 11 below.

TABLE 11

| Name of the antibody | $K_D$ to HuSema3A (pM) | $K_D$ to CynoSema3A (pM) | $K_D$ to MouseSema3A (pM) | $K_D$ to RatSema3A (pM) | $K_D$ to RabbitSema3A (pM) |
| --- | --- | --- | --- | --- | --- |
| Samsung scFv 1 | 359 | 89.0 | 105 | <20 | 112 |
| Samsung scFv 2 | 359 | 118 | 117 | <20 | 122 |
| Samsung scFv 3 | 296 | 68.0 | 88.8 | <20 | 59.5 |
| Antibody of the invention (clone I) | 34.7 | 35.0 | 35.0 | 23.5 | 40.1 |

43

Conclusion

The antibody of the invention has a higher binding affinity to human, cyno, mouse, or rabbit Sema3A than the 3 Samsung scFv as disclosed in WO2017074013.

Example 10: Comparison of Affinity of Two Antibodies According to the Invention

The inventors have developed two antibodies having the CDRs as depicted in SEQ ID NO: 1 to 6. The two antibodies vary in the Fc region in that:

one antibody comprises the combination L234A and L235A (antibody A), and the other antibody comprises the mutation H435A (antibody B), the residues being numbered according to the EU index of Kabat.

No statistical difference was shown in the binding affinity of both antibodies to human Sema3A having the CDRs as depicted in SEQ ID NO: 1 to 6. Therefore, the affinity to human Sema3A is maintained in antibodies directed against Sema3A according to the invention.

Example 11: Potency of a Commercially Available Antibody Directed Against Sema3A For sake of comparison, the inventors tested the cellular activity of a commercially available antibody targeting Sema3A. Said antibody is commercialised by Creative Biolabs under the reference "Anti-Human SEMA3A Therapeutic Antibody, Humanized (CAT #: TAB-556CL)". Said commercially available antibody will be referred to as the "Creative Biolabs antibody" in the following.

The Cellular activity of the Creative Biolabs antibody was assessed by a measure of cytoskeletal collapse in human retinal microvascular endothelial cells (HRMEC) with the same protocol disclosed in Example 3. Calculations and determination of potency were done 5h after stimulation.

Under these conditions, the Creative Biolabs antibody did not show any activity on the cytoskeletal collapse induced by Sema3A. The cytoskeletal collapse induced by Sema3A could indeed not be prevented by the Creative Biolabs antibody.

Therefore, the Creative Biolabs antibody proved not to prevent Sema3A-induced cytoskeletal collapse in retinal cells whereas, in the same conditions, the antibody of the invention does. This confirms the surprising and unexpected effect of the antibody of the invention.

The invention claimed is:

1. An anti-Sema3A antibody or an antigen-binding fragment thereof comprising:

a heavy chain variable region comprising the amino acid sequence of SEQ ID NO: 1 (H-CDR1); the amino acid sequence of SEQ ID NO: 2 (H-CDR2); and the amino acid sequence of SEQ ID NO: 3 (H-CDR3); and a light chain variable region comprising the amino acid sequence of SEQ ID NO: 4 (L-CDR1); the amino acid sequence of SEQ ID NO: 5 (L-CDR2); and the amino acid sequence of SEQ ID NO: 6 (L-CDR3).

2. The anti-Sema3A antibody or the antigen-binding fragment thereof according to claim 1, wherein the antibody or the antigen-binding fragment thereof comprises:
 a heavy chain variable region comprising the amino acid sequences of SEQ ID NO: 7, SEQ ID NO: 8, SEQ ID NO: 9 or SEQ ID NO: 10 and
 a light chain variable region comprising the amino acid sequence of SEQ ID NO: 11, SEQ ID NO: 12 or SEQ ID NO: 13.

3. The anti-Sema3A antibody or the antigen-binding fragment thereof according to claim 1, wherein the antibody or the antigen-binding fragment thereof comprises:
 a) a variable heavy chain and a variable light chain comprising the amino acid sequences of SEQ ID NO: 7 and SEQ ID NO: 11, respectively;
 b) a variable heavy chain and a variable light chain comprising the amino acid sequences of SEQ ID NO: 8 and SEQ ID NO: 11, respectively;
 c) a variable heavy chain and a variable light chain comprising the amino acid sequences of SEQ ID NO: 9 and SEQ ID NO: 12, respectively; or
 d) a variable heavy chain and a variable light chain comprising the amino acid sequences of SEQ ID NO: 10 and SEQ ID NO: 13, respectively.

4. The anti-Sema3A antibody or the antigen-binding fragment thereof according to claim 1, wherein the antibody or the antigen-binding fragment thereof comprises:
 a heavy chain comprising, the amino acid sequence of SEQ ID NO: 14, SEQ ID NO: 16, SEQ ID NO: 17 or SEQ ID NO: 19; and
 a light chain comprising, preferably consisting of, the amino acid sequence of SEQ ID NO: 15, SEQ ID NO: 18 or SEQ ID NO: 20.

5. The anti-Sema3A antibody or the antigen-binding fragment thereof according to claim 1, wherein the antibody or the antigen-binding fragment thereof comprises:
 a) a heavy chain comprising the amino acid sequence of SEQ ID NO: 14 and a light chain comprising the amino acid sequence of SEQ ID NO: 15;
 b) a heavy chain comprising the amino acid sequence of SEQ ID NO: 16 and a light chain comprising the amino acid sequence of SEQ ID NO: 15;
 c) a heavy chain comprising the amino acid sequence of SEQ ID NO: 17 and a light chain comprising the amino acid sequence of SEQ ID NO: 18; or
 d) a heavy chain comprising the amino acid sequence of SEQ ID NO: 19 and a light chain comprising the amino acid sequence of SEQ ID NO: 20.

6. A method for inhibiting the vasorepressive effect of SemaA3, comprising administering a pharmaceutically effective amount of the antibody or the antigen-binding fragment according to claim 1 to a patient in need thereof.

7. A method for improving revascularization of the retina, comprising administering a pharmaceutically effective amount of the antibody or the antigen-binding fragment according to claim 1 to a patient in need thereof.

8. A method for treating an eye or a retinal disease comprising administering a pharmaceutically effective amount of the antibody or the antigen-binding fragment according to claim 1 to a patient in need thereof.

9. The method according to claim 8, wherein said disease is selected from the group consisting of retinopathy, ischemic retinopathy, proliferative diabetic retinopathy, non-proliferative diabetic retinopathy, diabetic macular edema, diabetic macular ischemia, age-related macular degeneration, retinitis pigmentosa, inherited retinal dystrophy, myopic degeneration, retinal artery occlusions, endophthalmitis, uveitis, cystoid macular edema, optic neuropathies, glaucoma, retinal detachment, toxic retinopathy, radiation retinopathy, traumatic retinopathy, drug-induced retinal vasculopathy, retinal neovascularisation, polypoidal choroidal vasculopathy, retinal vasculitis, retinal microaneurysm, Fuch's dystrophy, macular telangiectasia, usher syndrome, and Stargardt disease.

10. The method according to claim 8, wherein said disease is selected from the group consisting of proliferative diabetic retinopathy, non-proliferative diabetic retinopathy, ischemic retinopathy, diabetic macular edema, diabetic macular ischemia, age-related macular degeneration, retinal neovascularization, glaucoma and choroidal neovascularization.

11. The method according to claim 8, wherein said disease is diabetic macular edema and/or diabetic macular ischemia.

12. The method according to claim 8, wherein:
 said disease is diabetic macular ischemia, and
 said antibody or an antigen-binding fragment promotes vascular regeneration within the ischemic retina (revascularisation) and prevents pathological neovascularization of the vitreous region of the eye.

13. The method according to claim 8, wherein:
 said disease is diabetic macular edema, and
 said antibody or an antigen-binding fragment reduces permeability of blood retinal barrier.

14. The method according to claim 13, wherein said antibody or an antigen-binding fragment inhibits Sema3A-induced permeability of the blood retinal barrier.

15. A pharmaceutical composition comprising an antibody or an antigen-binding fragment according to claim 1 and a pharmaceutically acceptable carrier.

16. The method according to claim 8, wherein said antibody or an antigen-binding fragment thereof is administered by a parenteral route, intravenous route, intravitreal route or subcutaneous route of administration.

17. The method according to claim 8, wherein said antibody or an antigen-binding fragment thereof is administered by intravitreal route.

18. An isolated polynucleotide comprising:
 a sequence encoding a heavy chain comprising any of SEQ ID NO: 14, SEQ ID NO: 16, SEQ ID NO: 17, or SEQ ID NO: 19 or a heavy chain variable region comprising any of SEQ ID NO: 7, SEQ ID NO: 8, SEQ ID NO: 9 or SEQ ID NO: 10; and
 a sequence encoding a light chain comprising any of SEQ ID NO: 15, SEQ ID NO: 18 or SEQ ID NO: 20 or a light chain variable region comprising any of SEQ ID NO: 11, SEQ ID NO: 12 or SEQ ID NO: 13.

19. An expression vector comprising the isolated polynucleotide of claim 18.

20. A host cell comprising the isolated polynucleotide according to claim 18.

21. A method for producing an anti-Sema3A antibody or an antigen-binding fragment thereof comprising:
 a) obtaining a host cell according to claim 20; and
 b) cultivating the host cell.

22. The method according to claim 21, further comprising recovering and purifying the antibody or the antigen-binding fragment thereof.

23. An anti-Sema3A antibody or an antigen-binding fragment thereof, wherein the antibody or the antigen-binding fragment thereof comprises a heavy chain comprising the amino acid sequence of SEQ ID NO: 14 and a light chain comprising the amino acid sequence of SEQ ID NO: 15.

24. An anti-Sema3A antibody or an antigen-binding fragment thereof, wherein the antibody or the antigen-binding fragment thereof comprises a heavy chain comprising the amino acid sequence of SEQ ID NO: 16 and a light chain comprising the amino acid sequence of SEQ ID NO: 15.

25. An anti-Sema3A antibody or an antigen-binding fragment thereof, wherein the antibody or the antigen-binding fragment thereof comprises a heavy chain comprising the amino acid sequence of SEQ ID NO: 17 and a light chain comprising the amino acid sequence of SEQ ID NO: 18.

26. An anti-Sema3A antibody or an antigen-binding fragment thereof, wherein the antibody or the antigen-binding fragment thereof comprises a heavy chain comprising the amino acid sequence of SEQ ID NO: 19 and a light chain comprising the amino acid sequence of SEQ ID NO: 20.

* * * * *

UNITED STATES PATENT AND TRADEMARK OFFICE
CERTIFICATE OF CORRECTION

| | | |
|---|---|---|
| PATENT NO. | : 11,267,880 B2 | Page 1 of 1 |
| APPLICATION NO. | : 16/869618 | |
| DATED | : March 8, 2022 | |
| INVENTOR(S) | : Thomas et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 0 days.

Signed and Sealed this
Twenty-ninth Day of November, 2022

Katherine Kelly Vidal
*Director of the United States Patent and Trademark Office*

SEQUENCE LISTING

```
<160> NUMBER OF SEQ ID NOS: 22

<210> SEQ ID NO 1
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR1

<400> SEQUENCE: 1

Ser Tyr Tyr Met Ser
1               5

<210> SEQ ID NO 2
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR2

<400> SEQUENCE: 2

Thr Ile Ile Lys Ser Gly Gly Tyr Ala Tyr Tyr Pro Asp Ser Val Lys
1               5                   10                  15

Asp

<210> SEQ ID NO 3
<211> LENGTH: 8
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: HCDR3

<400> SEQUENCE: 3
```

```
Gly Gly Gln Gly Ala Met Asp Tyr
1               5

<210> SEQ ID NO 4
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR1

<400> SEQUENCE: 4

Arg Ala Ser Gln Ser Ile Gly Asp Tyr Leu His
1               5                   10

<210> SEQ ID NO 5
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR2

<400> SEQUENCE: 5

Tyr Ala Ser Gln Ser Ile Ser
1               5

<210> SEQ ID NO 6
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: LCDR3

<400> SEQUENCE: 6

Gln Gln Gly Tyr Ser Phe Pro Tyr Thr
1               5

<210> SEQ ID NO 7
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 1

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80
```

Leu Gln Met Ser Ser Leu Arg Ala Glu Asp Thr Ala Val Tyr Tyr Cys
                    85                  90                  95

Val Arg Gly Gly Gln Gly Ala Met Asp Tyr Trp Gly Gln Gly Thr Thr
                100                 105                 110

Val Thr Val Ser Ser
        115

<210> SEQ ID NO 8
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 2

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
                20                  25                  30

Tyr Met Ser Trp Val Arg Gln Ala Pro Gly Lys Gly Leu Glu Trp Val
            35                  40                  45

Ser Thr Ile Ile Lys Ser Gly Gly Tyr Ala Tyr Tyr Pro Asp Ser Val
        50                  55                  60

Lys Asp Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                    85                  90                  95

Val Arg Gly Gly Gln Gly Ala Met Asp Tyr Trp Gly Gln Gly Thr Thr
                100                 105                 110

Val Thr Val Ser Ser
        115

<210> SEQ ID NO 9
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 3

<400> SEQUENCE: 9

Glu Val Gln Leu Val Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
                20                  25                  30

Tyr Met Ser Trp Val Arg Gln Ala Pro Gly Lys Gly Leu Glu Trp Val
            35                  40                  45

Ser Thr Ile Ile Lys Ser Gly Gly Tyr Ala Tyr Tyr Pro Asp Ser Val
        50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                    85                  90                  95

Val Lys Gly Gly Gln Gly Ala Met Asp Tyr Trp Gly Gln Gly Thr Thr

Val Thr Val Ser Ser
        115

<210> SEQ ID NO 10
<211> LENGTH: 117
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VH - variant 4

<400> SEQUENCE: 10

Glu Val Gln Leu Val Glu Ser Gly Gly Gly Leu Leu Gln Leu Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
50                  55                  60

Lys Asp Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Val Lys Gly Gly Gln Gly Ala Met Asp Tyr Trp Gly Gln Gly Thr Thr
            100                 105                 110

Val Thr Val Ser Ser
        115

<210> SEQ ID NO 11
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL - variant a

<400> SEQUENCE: 11

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
        50                  55                  60

Ser Gly Ser Gly Thr Asp Phe Thr Leu Thr Ile Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 12
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL - variant b

<400> SEQUENCE: 12

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 13
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: VL - variant c

<400> SEQUENCE: 13

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys
            100                 105

<210> SEQ ID NO 14
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain- Clone I

<400> SEQUENCE: 14

Glu Val Gln Leu Val Glu Ser Gly Gly Gly Leu Val Gln Pro Gly Gly
```

-continued

```
1               5                   10                  15
Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80

Leu Gln Met Ser Ser Leu Arg Ala Glu Asp Thr Ala Val Tyr Tyr Cys
                85                  90                  95

Val Arg Gly Gly Gln Gly Ala Met Asp Tyr Trp Gly Gln Gly Thr Thr
                100                 105                 110

Val Thr Val Ser Ser Ala Ser Thr Lys Gly Pro Ser Val Phe Pro Leu
            115                 120                 125

Ala Pro Ser Ser Lys Ser Thr Ser Gly Gly Thr Ala Ala Leu Gly Cys
        130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430
```

His Asn His Tyr Thr Gln Lys Ser Leu Ser Leu Ser Pro Gly
        435                 440                 445

<210> SEQ ID NO 15
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light Chain - Clone I

<400> SEQUENCE: 15

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Lys Tyr Ala Ser Gln Ser Ile Ser Gly Ile Pro Ala Arg Phe Ser Gly
    50                  55                  60

Ser Gly Ser Gly Thr Asp Phe Thr Leu Thr Ile Thr Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 16
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Heavy Chain - Clone II

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Tyr Met Ser Trp Val Arg Gln Ala Pro Gly Lys Gly Leu Glu Trp Val

```
            35                  40                  45
Ser Thr Ile Ile Lys Ser Gly Gly Tyr Ala Tyr Tyr Pro Asp Ser Val
 50                  55                  60

Lys Asp Arg Phe Thr Ile Ser Arg Asp Asn Ser Lys Asn Thr Leu Tyr
 65                  70                  75                  80

Leu Gln Met Ser Ser Leu Arg Ala Glu Asp Thr Ala Val Tyr Tyr Cys
                 85                  90                  95

Val Arg Gly Gly Gln Gly Ala Met Asp Tyr Trp Gly Gln Gly Thr Thr
                100                 105                 110

Val Thr Val Ser Ser Ala Ser Thr Lys Gly Pro Ser Val Phe Pro Leu
                115                 120                 125

Ala Pro Ser Ser Lys Ser Thr Ser Gly Gly Thr Ala Ala Leu Gly Cys
            130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
                180                 185                 190

Leu Gly Thr Gln Thr Tyr Ile Cys Asn Val Asn His Lys Pro Ser Asn
                195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
                260                 265                 270

Val Lys Phe Asn Trp Tyr Val Asp Gly Val Glu Val His Asn Ala Lys
            275                 280                 285

Thr Lys Pro Arg Glu Glu Gln Tyr Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
            420                 425                 430

His Asn His Tyr Thr Gln Lys Ser Leu Ser Leu Ser Pro Gly
            435                 440                 445

<210> SEQ ID NO 17
```

<211> LENGTH: 446
<212> TYPE: PRT
<213> ORGANISM: Artificial Sequence
<220> FEATURE:
<223> OTHER INFORMATION: Description of Artificial Sequence: Synthetic polypeptide
<220> FEATURE:
<223> OTHER INFORMATION: Heavy Chain - Clone III

<400> SEQUENCE: 17

```
Glu Val Gln Leu Val Glu Ser Gly Gly Gly Leu Val Gln Leu Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Val Lys Gly Gly Gln Gly Ala Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365
```

```
Val Lys Gly Phe Tyr Pro Ser Asp Ile Ala Val Glu Trp Glu Ser Asn
        370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Lys Leu Thr Val Asp Lys Ser Arg
                405                 410                 415

Trp Gln Gln Gly Asn Val Phe Ser Cys Ser Val Met His Glu Ala Leu
                420                 425                 430

His Asn His Tyr Thr Gln Lys Ser Leu Ser Leu Ser Pro Gly
                435                 440                 445

<210> SEQ ID NO 18
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light Chain - Clone III

<400> SEQUENCE: 18

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Ile Gly Asp Tyr
            20                  25                  30

Leu His Trp Tyr Gln Gln Lys Pro Gly Gln Ala Pro Arg Leu Leu Ile
        35                  40                  45

Tyr Tyr Ala Ser Gln Ser Ile Ser Gly Ile Pro Ala Arg Phe Ser Gly
50                  55                  60

Ser Gly Ser Gly Thr Asp Phe Thr Leu Thr Ile Ser Ser Leu Glu Pro
65                  70                  75                  80

Glu Asp Phe Ala Val Tyr Tyr Cys Gln Gln Gly Tyr Ser Phe Pro Tyr
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 19
<211> LENGTH: 446
<212> TYPE: PRT
<213> ORGANISM: Artificial Sequence
<220> FEATURE:
<223> OTHER INFORMATION: Description of Artificial Sequence: Synthetic
      polypeptide
```

<220> FEATURE:
<223> OTHER INFORMATION: Heavy Chain- Clone IV

<400> SEQUENCE: 19

Glu Val Gln Leu Val Glu Ser Gly Gly Gly Leu Leu Gln Leu Gly Gly
1               5                   10                  15

Ser Leu Arg Leu Ser Cys Ala Ala Ser Gly Phe Thr Phe Ser Ser Tyr
            20                  25                  30

Tyr Met Ser Trp Val Arg Gln Ala Pro Gly Lys Gly Leu Glu Trp Val
        35                  40                  45

Ser Thr Ile Ile Lys Ser Gly Gly Tyr Ala Tyr Tyr Pro Asp Ser Val
    50                  55                  60

Lys Asp Arg Phe Thr Ile Ser Arg Asp Asn Ser Lys Asn Thr Leu Asn
65                  70                  75                  80

Leu Gln Met Asn Ser Leu Arg Ala Glu Asp Thr Ala Val Tyr Tyr Cys
                85                  90                  95

Val Lys Gly Gly Gln Gly Ala Met Asp Tyr Trp Gly Gln Gly Thr Thr
            100                 105                 110

Val Thr Val Ser Ser Ala Ser Thr Lys Gly Pro Ser Val Phe Pro Leu
        115                 120                 125

Ala Pro Ser Ser Lys Ser Thr Ser Gly Gly Thr Ala Ala Leu Gly Cys
    130                 135                 140

Leu Val Lys Asp Tyr Phe Pro Glu Pro Val Thr Val Ser Trp Asn Ser
145                 150                 155                 160

Gly Ala Leu Thr Ser Gly Val His Thr Phe Pro Ala Val Leu Gln Ser
                165                 170                 175

Ser Gly Leu Tyr Ser Leu Ser Ser Val Val Thr Val Pro Ser Ser Ser
            180                 185                 190

Leu Gly Thr Gln Thr Tyr Ile Cys Asn Val Asn His Lys Pro Ser Asn
        195                 200                 205

Thr Lys Val Asp Lys Arg Val Glu Pro Lys Ser Cys Asp Lys Thr His
    210                 215                 220

Thr Cys Pro Pro Cys Pro Ala Pro Glu Ala Ala Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser His Glu Asp Pro Glu
            260                 265                 270

Val Lys Phe Asn Trp Tyr Val Asp Gly Val Glu Val His Asn Ala Lys
        275                 280                 285

Thr Lys Pro Arg Glu Glu Gln Tyr Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Ala Leu Pro Ala Pro Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Arg Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

```
Asp Gly Ser Phe Phe Leu Tyr Ser Lys Leu Thr Val Asp Lys Ser Arg
            405                 410                 415
Trp Gln Gln Gly Asn Val Phe Ser Cys Ser Val Met His Glu Ala Leu
        420                 425                 430
His Asn His Tyr Thr Gln Lys Ser Leu Ser Leu Ser Pro Gly
    435                 440                 445

<210> SEQ ID NO 20
<211> LENGTH: 214
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<223> OTHER INFORMATION: Light Chain - Clone IV

<400> SEQUENCE: 20

Glu Ile Val Leu Thr Gln Ser Pro Ala Thr Leu Ser Leu Ser Pro Gly
1               5                   10                  15
Glu Arg Ala Thr Leu Ser Cys Arg Ala Ser Gln Ser Ile Gly Asp Tyr
            20                  25                  30
Leu His Trp Tyr Gln Gln Lys Pro Gly Gln Ala Pro Arg Leu Leu Ile
        35                  40                  45
Lys Tyr Ala Ser Gln Ser Ile Ser Gly Ile Pro Ala Arg Phe Ser Gly
    50                  55                  60
Ser Gly Ser Gly Thr Asp Phe Thr Leu Thr Ile Ser Ser Leu Glu Pro
65                  70                  75                  80
Glu Asp Phe Ala Val Tyr Tyr Cys Gln Gln Gly Tyr Ser Phe Pro Tyr
                85                  90                  95
Thr Phe Gly Gly Gly Thr Lys Leu Glu Ile Lys Arg Thr Val Ala Ala
            100                 105                 110
Pro Ser Val Phe Ile Phe Pro Pro Ser Asp Glu Gln Leu Lys Ser Gly
        115                 120                 125
Thr Ala Ser Val Val Cys Leu Leu Asn Asn Phe Tyr Pro Arg Glu Ala
    130                 135                 140
Lys Val Gln Trp Lys Val Asp Asn Ala Leu Gln Ser Gly Asn Ser Gln
145                 150                 155                 160
Glu Ser Val Thr Glu Gln Asp Ser Lys Asp Ser Thr Tyr Ser Leu Ser
                165                 170                 175
Ser Thr Leu Thr Leu Ser Lys Ala Asp Tyr Glu Lys His Lys Val Tyr
            180                 185                 190
Ala Cys Glu Val Thr His Gln Gly Leu Ser Ser Pro Val Thr Lys Ser
        195                 200                 205
Phe Asn Arg Gly Glu Cys
    210

<210> SEQ ID NO 21
<211> LENGTH: 13
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<223> OTHER INFORMATION: Epitope

<400> SEQUENCE: 21

Asp Ser Thr Lys Asp Leu Pro Asp Asp Val Ile Thr Phe
```

<210> SEQ ID NO 22
<211> LENGTH: 751
<212> TYPE: PRT
<213> ORGANISM: Homo sapiens

<400> SEQUENCE: 22

```
Asn Tyr Gln Asn Gly Lys Asn Asn Val Pro Arg Leu Lys Leu Ser Tyr
1               5                   10                  15
Lys Glu Met Leu Glu Ser Asn Asn Val Ile Thr Phe Asn Gly Leu Ala
            20                  25                  30
Asn Ser Ser Ser Tyr His Thr Phe Leu Leu Asp Glu Gly Arg Ser Arg
        35                  40                  45
Leu Tyr Val Gly Ala Lys Asp His Ile Phe Ser Phe Asp Leu Val Asn
    50                  55                  60
Ile Lys Asp Phe Gln Lys Ile Val Trp Pro Val Ser Tyr Thr Arg Arg
65                  70                  75                  80
Asp Glu Cys Lys Trp Ala Gly Lys Asp Ile Leu Lys Glu Cys Ala Asn
                85                  90                  95
Phe Ile Lys Val Leu Lys Ala Tyr Asn Gln Thr His Leu Tyr Ala Cys
            100                 105                 110
Gly Thr Gly Ala Phe His Pro Ile Cys Thr Tyr Ile Glu Ile Gly His
        115                 120                 125
His Pro Glu Asp Asn Ile Phe Lys Leu Glu Asn Ser His Phe Glu Asn
    130                 135                 140
Gly Arg Gly Lys Ser Pro Tyr Asp Pro Lys Leu Leu Thr Ala Ser Leu
145                 150                 155                 160
Leu Ile Asp Gly Glu Leu Tyr Ser Gly Thr Ala Ala Asp Phe Met Gly
                165                 170                 175
Arg Asp Phe Ala Ile Phe Arg Thr Leu Gly His His His Pro Ile Arg
            180                 185                 190
Thr Glu Gln His Asp Ser Arg Trp Leu Asn Asp Pro Lys Phe Ile Ser
        195                 200                 205
Ala His Leu Ile Ser Glu Ser Asp Asn Pro Glu Asp Asp Lys Val Tyr
    210                 215                 220
Phe Phe Phe Arg Glu Asn Ala Ile Asp Gly Glu His Ser Gly Lys Ala
225                 230                 235                 240
Thr His Ala Arg Ile Gly Gln Ile Cys Lys Asn Asp Phe Gly Gly His
                245                 250                 255
Arg Ser Leu Val Asn Lys Trp Thr Thr Phe Leu Lys Ala Arg Leu Ile
            260                 265                 270
Cys Ser Val Pro Gly Pro Asn Gly Ile Asp Thr His Phe Asp Glu Leu
        275                 280                 285
Gln Asp Val Phe Leu Met Asn Phe Lys Asp Pro Lys Asn Pro Val Val
    290                 295                 300
Tyr Gly Val Phe Thr Thr Ser Ser Asn Ile Phe Lys Gly Ser Ala Val
305                 310                 315                 320
Cys Met Tyr Ser Met Ser Asp Val Arg Arg Val Phe Leu Gly Pro Tyr
                325                 330                 335
Ala His Arg Asp Gly Pro Asn Tyr Gln Trp Val Pro Tyr Gln Gly Arg
            340                 345                 350
Val Pro Tyr Pro Arg Pro Gly Thr Cys Pro Ser Lys Thr Phe Gly Gly
        355                 360                 365
```

-continued

```
Phe Asp Ser Thr Lys Asp Leu Pro Asp Asp Val Ile Thr Phe Ala Arg
    370             375             380
Ser His Pro Ala Met Tyr Asn Pro Val Phe Pro Met Asn Asn Arg Pro
385             390             395             400
Ile Val Ile Lys Thr Asp Val Asn Tyr Gln Phe Thr Gln Ile Val Val
            405             410             415
Asp Arg Val Asp Ala Glu Asp Gly Gln Tyr Asp Val Met Phe Ile Gly
            420             425             430
Thr Asp Val Gly Thr Val Leu Lys Val Val Ser Ile Pro Lys Glu Thr
            435             440             445
Trp Tyr Asp Leu Glu Glu Val Leu Leu Glu Glu Met Thr Val Phe Arg
    450             455             460
Glu Pro Thr Ala Ile Ser Ala Met Glu Leu Ser Thr Lys Gln Gln Gln
465             470             475             480
Leu Tyr Ile Gly Ser Thr Ala Gly Val Ala Gln Leu Pro Leu His Arg
            485             490             495
Cys Asp Ile Tyr Gly Lys Ala Cys Ala Glu Cys Cys Leu Ala Arg Asp
            500             505             510
Pro Tyr Cys Ala Trp Asp Gly Ser Ala Cys Ser Arg Tyr Phe Pro Thr
    515             520             525
Ala Lys Arg Arg Thr Arg Arg Gln Asp Ile Arg Asn Gly Asp Pro Leu
530             535             540
Thr His Cys Ser Asp Leu His His Asp Asn His His Gly His Ser Pro
545             550             555             560
Glu Glu Arg Ile Ile Tyr Gly Val Glu Asn Ser Ser Thr Phe Leu Glu
            565             570             575
Cys Ser Pro Lys Ser Gln Arg Ala Leu Val Tyr Trp Gln Phe Gln Arg
            580             585             590
Arg Asn Glu Glu Arg Lys Glu Glu Ile Arg Val Asp Asp His Ile Ile
            595             600             605
Arg Thr Asp Gln Gly Leu Leu Leu Arg Ser Leu Gln Gln Lys Asp Ser
    610             615             620
Gly Asn Tyr Leu Cys His Ala Val Glu His Gly Phe Ile Gln Thr Leu
625             630             635             640
Leu Lys Val Thr Leu Glu Val Ile Asp Thr Glu His Leu Glu Glu Leu
            645             650             655
Leu His Lys Asp Asp Asp Gly Asp Gly Ser Lys Thr Lys Glu Met Ser
            660             665             670
Asn Ser Met Thr Pro Ser Gln Lys Val Trp Tyr Arg Asp Phe Met Gln
            675             680             685
Leu Ile Asn His Pro Asn Leu Asn Thr Met Asp Glu Phe Cys Glu Gln
    690             695             700
Val Trp Lys Arg Asp Arg Lys Gln Arg Arg Gln Arg Pro Gly His Thr
705             710             715             720
Pro Gly Asn Ser Asn Lys Trp Lys His Leu Gln Glu Asn Lys Lys Gly
            725             730             735
Arg Asn Arg Arg Thr His Glu Phe Glu Arg Ala Pro Arg Ser Val
            740             745             750
```